(12) United States Patent
Nelson et al.

(10) Patent No.: US 10,472,620 B2
(45) Date of Patent: *Nov. 12, 2019

(54) METHOD, SUBSTRATE AND DEVICE FOR SEPARATING NUCLEIC ACIDS

(71) Applicant: General Electric Company, Schenectady, NY (US)

(72) Inventors: John Richard Nelson, Clifton Park, NY (US); David Roger Moore, Rexford, NY (US); Robert Scott Duthie, Schenectady, NY (US); Matthew Jeremiah Misner, Delanson, NY (US); Gregory Andrew Grossmann, Halfmoon, NY (US); Elizabeth Marie Dees, Ballston Lake, NY (US); Patrick McCoy Spooner, Slingerlands, NY (US); Erik Leeming Kvam, Niskayuna, NY (US); Andrew Arthur Paul Burns, Niskayuna, NY (US); Vicki Herzl Watkins, Alplaus, NY (US)

(73) Assignee: General Electric Company, Schenectady, NY (US)

( * ) Notice: Subject to any disclaimer, the term of this patent is extended or adjusted under 35 U.S.C. 154(b) by 92 days.

This patent is subject to a terminal disclaimer.

(21) Appl. No.: 14/321,160

(22) Filed: Jul. 1, 2014

(65) Prior Publication Data

US 2016/0002621 A1 Jan. 7, 2016

(51) Int. Cl.
*C12P 19/34* (2006.01)
*C12N 15/10* (2006.01)

(52) U.S. Cl.
CPC .............. *C12N 15/1006* (2013.01)

(58) Field of Classification Search
USPC .......... 435/6.1, 6.11, 6.12, 91.1, 91.2, 91.51, 435/183; 436/94, 501; 536/23.1, 24.3,
(Continued)

(56) References Cited

U.S. PATENT DOCUMENTS 5,955,351 A 9/1999 Gerdes et al.
6,037,127 A 3/2000 Ebersole et al.
(Continued)

FOREIGN PATENT DOCUMENTS

CN 103667253 A 3/2014
EP 2369015 B1 4/2014
(Continued)

OTHER PUBLICATIONS

"Guanidinium thiocyanate" from Wikipedia, the free encyclopedia. Printed on Feb. 15, 2017.*
(Continued)

*Primary Examiner* — Frank W Lu
(74) *Attorney, Agent, or Firm* — Eversheds Sutherland (US) LLP

(57) ABSTRACT

A method is provided herein, the method includes: applying a sample comprising target nucleic acids to a sample application zone of a substrate; and flowing a nucleic acid amplification reaction mixture across a length of the substrate through the sample application zone to amplify the target nucleic acid forming a nucleic acid amplification product; wherein the target nucleic acid having a first molecular weight is substantially immobilized at the sample application zone and wherein the amplification product having a second molecular weight migrates away from the sample application zone. An associated device is also provided.

31 Claims, 11 Drawing Sheets

(58) Field of Classification Search
USPC .............................................. 536/24.33, 25.3
See application file for complete search history.

(56) References Cited

U.S. PATENT DOCUMENTS

| | | |
|---|---|---|
| 6,221,603 B1 | 4/2001 | Mahtani |
| 6,255,082 B1 | 7/2001 | Lizard |
| 6,608,186 B1 | 8/2003 | Miculka et al. |
| 7,153,955 B2 | 12/2006 | Miculka et al. |
| 7,358,047 B2 | 4/2008 | Hafner et al. |
| 7,589,187 B2 | 9/2009 | McCall et al. |
| 7,618,776 B2 | 11/2009 | Lizardi |
| 7,858,396 B2 | 12/2010 | Corstjens et al. |
| 8,043,811 B2 | 10/2011 | Danks et al. |
| 8,062,850 B2 | 11/2011 | Piepenburg et al. |
| 2003/0032024 A1 | 2/2003 | Lizardi |
| 2003/0087271 A1 | 5/2003 | Ebersole et al. |
| 2003/0190608 A1 | 10/2003 | Blackburn |
| 2004/0110167 A1 | 6/2004 | Gerdes et al. |
| 2005/0112636 A1 | 5/2005 | Hurt et al. |
| 2005/0227275 A1 | 10/2005 | Jung et al. |
| 2006/0160078 A1 | 7/2006 | Cardy et al. |
| 2007/0104962 A1 | 5/2007 | Laas et al. |
| 2009/0047673 A1 | 2/2009 | Cary |
| 2009/0143570 A1 | 6/2009 | Jiang et al. |
| 2009/0148933 A1 | 6/2009 | Battrell et al. |
| 2009/0186344 A1 | 7/2009 | Farinas |
| 2010/0190179 A1 | 7/2010 | Nilsen |
| 2011/0117540 A1 | 5/2011 | Cary |
| 2011/0171652 A1 | 7/2011 | You |
| 2011/0220502 A1 | 9/2011 | Selden et al. |
| 2011/0244467 A1 | 10/2011 | Haswell |
| 2011/0287951 A1 | 11/2011 | Emmert-Buck et al. |
| 2011/0294167 A1 | 12/2011 | McEwan et al. |
| 2012/0015358 A1 | 1/2012 | Scarr et al. |
| 2013/0210025 A1 | 8/2013 | Babu et al. |
| 2013/0230846 A1 | 9/2013 | Babu et al. |
| 2013/0295583 A1 | 11/2013 | Babu et al. |
| 2014/0039177 A1 | 2/2014 | Nelson et al. |
| 2014/0093878 A1 | 4/2014 | Nelson et al. |
| 2014/0113839 A1 | 4/2014 | Wu et al. |
| 2014/0162244 A1 | 6/2014 | Bau et al. |
| 2014/0272939 A1 | 9/2014 | Aghvanyan et al. |

FOREIGN PATENT DOCUMENTS

| | | |
|---|---|---|
| WO | 03066817 A2 | 8/2003 |
| WO | 2006074162 A2 | 7/2006 |

OTHER PUBLICATIONS

Nelson et al., filed Dec. 11, 2014, U.S. Appl. No. 14/566,865.

Nelson et al., filed Jul. 1, 2014, U.S. Appl. No. 14/321,235.

International Search Report and Written Opinion issued in connection with related PCT Application No. PCT/US15/63468 dated Feb. 25, 2016.

Rohrman et al., "A Lateral Flow Assay for Quantitative Detection of Amplified Hiv-1 Rna", Plos One, 2012, 8 Pages.

Cannon et al., "Quantitative molecular hybridization on nylon membranes", Anal Biochem, vol. 149, No. 1, 1 Page, Aug. 1985.

Twomey et al., "Parameters affecting hybridization of nucleic acids blotted onto nylon or nitrocellulose membranes", Biotechniques, vol. 8, No. 5, 1 Page, May 1990.

Baner., "Signal amplification of padlock probes by rolling circle replication", Nucleic acid research, vol. 26, No. 22, pp. 5073-5078, Oct. 1998.

Thomas et al., "Amplification of Padlock Probes for DNA Diagnostics by Cascade Rolling Circle Amplification or the Polymerase Chain Reaction", Archives of pathology and laboratory medicine, vol. 123, No. 12, pp. 1170-1176, Dec. 1999.

Brown, "Southern Blotting", Curr Protoc Immunol, Chapter 10: Unit 10.6A, 1 Page, May 2001.

Pongsuchart et al., "Sensitivity enhancement of nucleic acid detection by lateral flow strip test using UV crosslink method", Asian Biomedicine, vol. 6, No. 3, pp. 459-463, Jun. 2012.

PCT Search Report and Written Opinion from PCT Application No. PCT/US2015/038028 dated Oct. 28, 2015.

PCT Search Report and Written Opinion from PCT Application No. PCT/US2015/036981 dated Nov. 24, 2015.

U.S. Non-Final office Action issued in connection with Related U.S. Appl. No. 14/566,865 dated Mar. 10, 2017.

U.S. Final office Action issued in connection with Related U.S. Appl. No. 14/566,865 dated Aug. 24, 2017.

Kersting, S., et al., "Rapid detection of Plasmodium falciparum with isothermal recombinase polymerase amplification and lateral flow analysis," Malaria Journal, vol. 13, Issue 1, pp. 99-1-99-9 (Mar. 2014).

Extended European Search Report and Opinion issued in connection with corresponding EP Application No. 15816060.6 dated Oct. 26, 2017.

\* cited by examiner

METHOD, SUBSTRATE AND DEVICE FOR SEPARATING NUCLEIC ACIDS

This invention was made with Government support under grant number HR0011-11-2-0007, held by the University of Washington awarded by the Defense Advanced Research Projects Agency (DARPA). The Government has certain rights in the invention.

FIELD

The invention generally relates to methods and substrates for amplifying target nucleic acids followed by separating the amplified nucleic acids from the target.

BACKGROUND

Preparation and manipulation of high quality nucleic acids are primary requirements for a variety of applications, such as analyte-detection, sensing, forensic and diagnostic applications, genome sequencing, and the like. Various applications of nucleic acids are typically preceded by a purification process to eliminate unwanted contaminants from the nucleic acids, which may interfere in downstream applications. Techniques including gel electrophoresis, capillary electrophoresis or electrophoresis in microfluidic or microanalytical devices, which are mainstay in molecular and cell biology and enable purification and separation of specific nucleic acids.

The separation of nucleic acids provide information on size of the nucleic acids, which is useful for predicting a number of genetic disorders, such as genetic pre-dispositions or acquired mutations/local rearrangements for deoxyribonucleic acid (DNA). The ribonucleic acid (RNA) profiles represent "snap shots" of the cell's biology, since they are continuously changing in response to the surrounding environment.

In some applications, nucleic acid analysis requires sample-preparation involving multiple steps, such as collection, separation or purification of the nucleic acids from a biological sample. A simplified method for preparing nucleic acid sample for subsequent analysis is highly desirable. A simultaneous separation and amplification of nucleic acids is especially required when the quantity of the biological sample is less, for example, the sample procured for biopsy or a sample collected for forensic application.

Different technologies have been developed to separate nucleic acids from a liquid sample using a substrate, which includes: separating nucleic acids from a sample by flowing the sample along a bibulous membrane to distribute along the length of the membrane. In another method, at least two cellular components (such as, genomic DNA, RNA and proteins) is separated, wherein an aqueous solution including the cellular components applied to multiple mineral supports followed by washing. In many of these methods, the substrate requires a washing step with a buffer or a solution, which is not compatible with the subsequent process steps. The washing buffer needs to remove from the substrate before executing the subsequent steps. These methods are time consuming and complex as they require multiple steps (such as washing or elution) or multiple substrates.

The increased use of nucleic acids requires fast, simple and reliable methods and systems for separating nucleic acids.

BRIEF DESCRIPTION

In one embodiment, a method comprises applying a sample comprising target nucleic acids to a sample application zone of a substrate; and flowing a nucleic acid amplification reaction mixture across a length of the substrate through the sample application zone to amplify the target nucleic acid forming a nucleic acid amplification product. The target nucleic acid having a first molecular weight is substantially immobilized at the sample application zone and the amplification product having a second molecular weight migrates away from the sample application zone.

In another embodiment, a method comprises applying a sample comprising target nucleic acids to a sample application zone of a substrate; flowing a nucleic acid amplification reaction mixture across a length of the substrate through the sample application zone to amplify the target nucleic acid forming a nucleic acid amplification product; and separating the target nucleic acids from the amplified nucleic acids, wherein the target nucleic acid having a first molecular weight is substantially immobilized at the sample application zone and the amplification product having a second molecular weight migrates away from the sample application zone; wherein the target nucleic acids are amplified, and separated without a washing step.

In one embodiment of substrate, the substrate comprises a sample application zone for applying a sample comprising a target nucleic acid having a first molecular weight and flowing an amplification reaction mixture along the length of the substrate through the sample application zone forming a nucleic acid amplification product having a second molecular weight; and a detection zone for separating the nucleic acid amplification product having second molecular weight from the target nucleic acids having first molecular weight according to molecular weights of the amplified nucleic acids and target nucleic acids.

In yet another embodiment, a device, comprises a substrate, comprising: a sample application zone for applying a target nucleic acid sample and flowing an amplification reaction mixture along the length of the substrate through the sample application zone forming a nucleic acid amplification product; and a detection zone for separating the nucleic acid amplification product from the target nucleic acids according to molecular weights of the amplified nucleic acids and target nucleic acids; and an amplification reagent reservoir.

BRIEF DESCRIPTION OF THE DRAWINGS

FIG. 10 B illustrates an electrophoresis image to determine lateral flow of target DNA and amplicons obtained in a flow diagram of FIG. 10A, example 5.

FIG. 10 C illustrates a gel electrophoresis image to determine a lateral flow of non-template control (NTC) obtained in flow diagram of FIG. 10A, example 6.

FIG. 11 B is an image that illustrates detection of amplicons when compared with a substrate with no cell.

DETAILED DESCRIPTION

Figure 1:
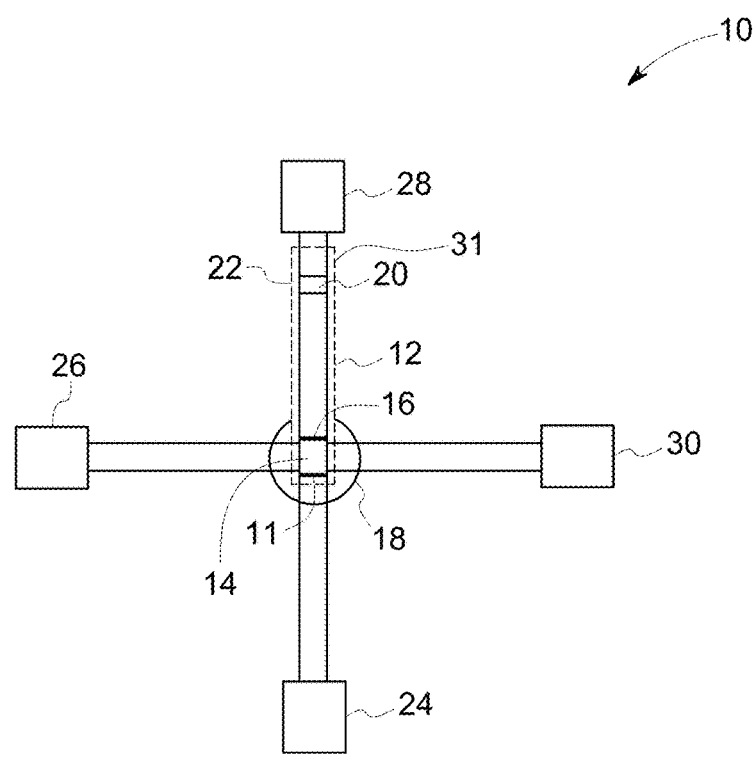
FIG. 1 illustrates a schematic diagram of a device in accordance with an example of an embodiment of the invention.

Various embodiments provide suitable methods and substrates for extraction of nucleic acids from a biological sample, followed by amplification and separation of the nucleic acid amplicons from each other and/or from unwanted contaminants based on molecular weights of different nucleic acid (amplicon) species or contaminants. The substrate is configured to collect a biological sample, extract nucleic acids from the sample followed by amplification and separation on the same substrate. The eluted nucleic acids are used in various downstream analysis or applications.

To more clearly and concisely describe the subject matter of the claimed invention, the following definitions are provided for specific terms, which are used in the following description and the appended claims. Throughout the specification, exemplification of specific terms should be considered as non-limiting examples.

The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Where necessary, ranges have been supplied, and those ranges are inclusive of all sub-ranges there between.

The term "nucleic acid" as referred to herein comprises all forms of DNA (e.g. genomic DNA, mtDNA) or RNA (mRNA, tRNA, rRNA, small RNA, siRNA, miRNA, non-coding RNA, animal RNA, plant RNA, viral RNA or bacterial RNA), as well as recombinant RNA and DNA molecules or analogues of DNA or RNA generated using nucleotide analogues. The nucleic acids may be single stranded or double stranded. The nucleic acids may include the coding or non-coding strands. The term also comprises fragments of nucleic acids, such as naturally occurring RNA or DNA which may be recovered using the extraction methods disclosed. Nucleic acid may also refer to a portion of a nucleic acid (e.g., RNA or DNA). The extracted nucleic acids may further comprise peptide nucleic acids (PNA).

Separated nucleic acids may comprise single type of nucleic acids or two or more different types of nucleic acids. The nucleic acids may be single-stranded, double-stranded, linear or circular. Molecular weights of separated nucleic acids are also not limited, may be optional in a range from several base pairs (bp) to several mega base pair (Mbp).

As used herein, the term "target nucleic acid" refers to a nucleic acid (such as DNA or RNA) sequence of either natural or synthetic origin that is desired to be amplified in an amplification reaction. The target nucleic acid may be obtained from a biological sample in vivo or in vitro. For example, the target nucleic acid may be obtained from a bodily fluid (e.g., blood, blood plasma, serum, or urine), an organ, a tissue, a cell, a sectional portion of an organ or tissue, a cell isolated from a biological subject (e.g., a region containing diseased cells, or circulating tumor cells), a forensic sample or an ancient sample. The biological sample that contains, or is suspected to contain, the target nucleic acid may be of eukaryotic origin, prokaryotic origin, viral origin or bacteriophage origin. For example, the target nucleic acid may be obtained from an insect, a protozoa, a bird, a fish, a reptile, a mammal (e.g., rat, mouse, cow, dog, guinea pig, or rabbit), or a primate (e.g., chimpanzee or human). The target nucleic acid may also be a complementary DNA (cDNA) that is generated from an RNA template (e.g., mRNA, ribosomal RNA) using a reverse transcriptase enzyme. A DNA product generated by another reaction, such as a ligation reaction, a PCR reaction, or a synthetic DNA may also serve as a suitable target nucleic acid. The target nucleic acid may be dispersed in solution or may be immobilized on a solid support, such as in blots, arrays, glass slides, microtiter plates, beads or ELISA plates. A target DNA or the entire region of a target DNA may be amplified by a DNA polymerase in a DNA amplification reaction to produce amplification products or amplicons.

As used herein, the term "sample application zone" refers to an area on a substrate, wherein a sample is applied to that area or zone of the substrate for further processing. The sample application zone is a part of the same substrate. In some embodiments the sample application zone may comprise impregnated reagents, such as stabilizing reagents or cell lysis reagents. The sample application zone may be a paper comprising reagents disposed on the substrate.

As used herein, the term "detection zone" refers to an area on a substrate, wherein the nucleic acids of a sample is separated according to its molecular weight at the detection zone of the substrate. The detection zone is a part of the same substrate. In some embodiments, the detection zone may comprise impregnated reagents, such as stabilizing reagents or buffer reagents. The detection zone may be a paper comprising reagents disposed on the substrate.

"Amplicons" or "amplification product" may include multiple copies of the target nucleic acid or multiple copies of sequences that are complementary to the target nucleic acid. The target nucleic acid, such as DNA acts as a template in a DNA amplification reaction to produce amplicons. Either a portion of a target DNA or the entire region of a target DNA may be amplified by a DNA polymerase in a DNA amplification reaction to produce amplification products or amplicons.

As used herein, the term "substantially immobilized" refers to a quantity of nucleic acids having certain molecular weights, which are positioned around a particular positioning portion. The immobilization of the nucleic acids may occur due to higher molecular weight of the nucleic acids. The nucleic acids having higher molecular weight typically have lower mobility while flowing a buffer along the length of the substrate. The substantial quantity of nucleic acids may be represented as the percentage of the total amount of nucleic acids having a particular molecular weights in the sample solution immobilize at a particular position. For example, substantially the nucleic acids with first molecular weight means 90% of the total target nucleic acids applied to the substrate immobilized at the substrate at or around the sample application zone.

As used herein the term "oligonucleotide" refers to an oligomer of nucleotides. A nucleotide may be represented by its letter designation using alphabetical letters corresponding to its nucleoside. For example, A denotes adenosine, C denotes cytidine, G denotes guanosine, U denotes uridine, and T denotes thymidine (5-methyl uridine). W denotes either A or T/U, and S denotes either G or C. N represents a random nucleoside and may be any of A, C, G, or T/U. A star (*) sign preceding a letter designation denotes that the nucleotide designated by the letter is a phosphorothioate-modified nucleotide. For example, *N represents a phosphorothioate-modified random nucleotide. A plus (+) sign preceding a letter designation denotes that the nucleotide designated by the letter is a locked nucleic acid (LNA) nucleotide. For example, +A represents an adenosine LNA nucleotide, and +N represents a locked random nucleotide. The oligonucleotide may be a DNA oligonucleotide, an RNA oligonucleotide or a DNA-RNA chimeric sequence. Whenever an oligonucleotide is represented by a sequence of letters, the nucleotides are in 5'→3' order from left to right. For example, an oligonucleotide represented by a letter sequence $(W)_x(N)_y(S)_z$, wherein x=2, y=3 and z=1, represents an oligonucleotide sequence WWNNNS, wherein W is the 5' terminal nucleotide and S is the 3' terminal nucleotide ("Terminal nucleotide" refers to a nucleotide that is located at a terminal position of an oligonucleotide sequence. The terminal nucleotide that is located at a 3' terminal position is referred as a 3' terminal nucleotide, and the terminal nucleotide that is located at a 5' terminal position is referred as a 5' terminal nucleotide).

As used herein the dNTP mixture refers to a mixture deoxyribonucleoside triphosphates, where N is a random nucleotide including any of A, C, G, or T/U.

As used herein, "primer", or "primer sequence" refers to a short linear oligonucleotide that hybridizes to a target nucleic acid sequence (e.g., a deoxyribonucleic acid (DNA)) to prime a nucleic acid amplification reaction. The primer may be a ribonucleic acid (RNA) oligonucleotide, a DNA oligonucleotide, or a chimeric sequence. The primer may contain natural, synthetic, or modified nucleotides. Both the upper and lower limits of the length of the primer are empirically determined. The lower limit on primer length is the minimum length that is required to form a stable duplex upon hybridization with the target nucleic acid under nucleic acid amplification reaction conditions. Very short primers (usually less than 3-4 nucleotides long) do not form thermodynamically stable duplexes with target nucleic acids under such hybridization conditions. The upper limit is often determined by the possibility of having a duplex formation in a region other than the pre-determined nucleic acids sequences in the target nucleic acids. As a non-limiting example, suitable primer lengths are often in the range of about 4 to about 40 nucleotides long. A primer may also be used to capture a nucleic acid sequence.

As used herein, the terms "amplification", "nucleic acid amplification", or "amplifying" refer to the production of multiple copies of a nucleic acid template, or the production of multiple nucleic acid sequence copies that are complementary to the nucleic acid template.

As used herein, "multiple displacement amplification" (MDA) refers to a nucleic acid amplification method, wherein the amplification involves the steps of annealing multiple primers to a denatured nucleic acid followed by DNA synthesis in which downstream double stranded DNA region(s) which would block continued synthesis is disrupted by a strand displacement nucleic acid synthesis through these regions. As synthesis proceeds through an area of double stranded DNA, and the synthesis of the new strand occurs while displacing the existing strand, there is a net increase in that sequence of DNA, or DNA amplification. This is termed as "strand displacement amplification", which occurs when one strand is displaced by the synthesis of a new strand. As nucleic acid is synthesized by strand displacement, single stranded DNA is generated by the strand displacement, and as a result, a gradually increasing number of priming events occur, forming a network of hyper-branched nucleic acid structures. MDA is highly useful for whole-genome amplification for generating high-molecular weight DNA from a small amount of genomic DNA sample with limited sequence bias. Any strand displacing nucleic acid polymerase that has a strand displacement activity apart from its nucleic acid synthesis activity (e.g., Phi29 DNA polymerase or a large fragment of the Bst DNA polymerase) may be used in MDA. MDA is often performed under isothermal reaction conditions, using random primers for achieving amplification with limited sequence bias.

As used herein, the term "rolling circle amplification (RCA)" refers to a nucleic acid amplification reaction that amplifies a circular nucleic acid template (e.g., single stranded DNA circles) via a rolling circle mechanism. RCA is initiated by the hybridization of a primer to a circular, often single-stranded, nucleic acid template. The nucleic acid polymerase then extends the primer that is hybridized to the circular nucleic acid template by continuously progressing around the circular nucleic acid template to replicate the sequence of the nucleic acid template over and over again (rolling circle mechanism). RCA typically produces concatamers comprising tandem repeat units of the circular nucleic acid template sequence complement.

As used herein, the term "DNA polymerase" refers to an enzyme that synthesizes a DNA strand de novo using a nucleic acid strand as a template. DNA polymerase uses an existing DNA or RNA as the template for DNA synthesis and catalyzes the polymerization of deoxyribonucleotides alongside the template strand, which it reads. The newly synthesized DNA strand is complementary to the template strand. DNA polymerase can add free nucleotides only to the 3'-hydroxyl end of the newly forming strand. It synthesizes oligonucleotides via transfer of a nucleoside monophosphate from a deoxyribonucleoside triphosphate (dNTP) to the 3'-hydroxyl group of a growing oligonucleotide chain. This results in elongation of the new strand in a 5'→3' direction. Since DNA polymerase can only add a nucleotide onto a pre-existing 3'-OH group, to begin a DNA synthesis reaction, the DNA polymerase needs a primer to which it can add the first nucleotide. Suitable primers comprise oligonucleotides of RNA or DNA or nucleotide analogs. The DNA polymerases may be a naturally occurring DNA polymerases or a variant of natural enzyme having the above-mentioned activity. For example, it may include a DNA polymerase having a strand displacement activity, a DNA polymerase lacking 5'→3' exonuclease activity, a DNA polymerase having a reverse transcriptase activity, or a DNA polymerase having an exonuclease activity.

As used herein, the terms "strand displacing nucleic acid polymerase" or "a polymerase having strand displacement activity" refer to a nucleic acid polymerase that has a strand displacement activity apart from its nucleic acid synthesis activity. A strand displacing nucleic acid polymerase can continue nucleic acid synthesis on the basis of the sequence of a nucleic acid template strand by reading the template strand while displacing a complementary strand that is annealed to the template strand. The strand displacing nucleic acid polymerase includes DNA polymerase, RNA polymerase, and reverse transcriptase.

The term, "reducing agents" as referred to herein include any chemical species that provides electrons to another chemical species. A variety of reducing agents are known in the art. Examples of reducing agents include dithiothreitol (DTT), 2-mercaptoethanol (2-ME), and tris(2-carboxyethyl) phosphine (TCEP). Moreover, any combination of these or other reducing agents may be used. In particular embodiments, the reducing agent is TCEP.

The term "amplification buffer" as used herein includes, but is not limited to, 2-Amino-2-hydroxymethyl-propane-1, 3-diol (Tris), 2-(N-morpholino) ethanesulfonic acid (MES), 3-(N-morpholino)propanesulfonic acid (MOPS), citrate buffers, 4-(2-hydroxyethyl)-1-piperazineethanesulfonic acid (HEPES), and phosphate buffers. The amplification buffer further includes, for example, Tris-HCl, diammonium sulphate, monovalent cation (such as KCl), divalent cation (such as $MgSO_4$) or Tween® 20. This list of potential buffers is for illustrative purposes only. The pH of the buffer is typically titrated in the range of 6 to 8. In some embodiments, the buffer comprises dNTPs, BSA or combination thereof.

The term "separate, separating or separation" used herein indicates the act or action to isolate or purify nucleic acids from unwanted contaminants of a sample solution and/or from each other according to molecular weights.

The term "biological sample" is used in a broad sense and is intended to include a variety of physiological or clinical biological sources that include nucleic acids. Such sources include, without limitation, whole tissues, including biopsy materials and aspirates; in vitro cultured cells, including primary and secondary cells, transformed cell lines, and tissue and blood cells; body fluids such as urine, sputum, semen, secretions, eye washes and aspirates, lung washes and aspirates; media from DNA or RNA synthesis; mixtures of chemically or biochemically synthesized DNA or RNA; fungal and plant tissues, such as leaves, roots, stems, and caps; microorganisms and viruses that may be present on or in a biological sample; bacterial cells; and any other source in which DNA and/or RNA is or may be in.

The sample solution is a solution comprising either or both of DNA and RNA, or, cells, cell components or cell extracts which comprise either or both of DNA and RNA, dissolved, suspended, mixed or otherwise included therein. The sample solution may be a solution prepared from a biological sample.

One or more embodiments of a method are provided, wherein the method comprises applying a sample comprising target nucleic acids to a sample application zone of a substrate; and flowing a nucleic acid amplification reaction mixture across a length of the substrate through the sample application zone to amplify the target nucleic acid to form a nucleic acid amplification product or amplicon. The target nucleic acid having a first molecular weight is substantially immobilized at the sample application zone and the amplification product having a second molecular weight migrates away from the sample application zone.

Figure 6:
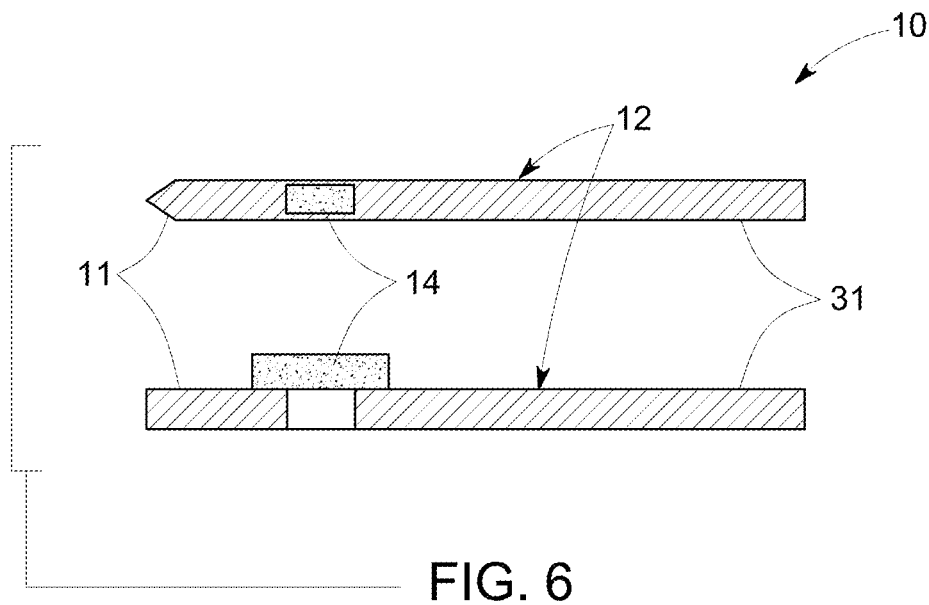
FIG. 6 illustrates top view (top) and side view (bottom) of a schematic diagram of a substrate in accordance with one embodiment of the invention.

As noted, the sample is applied to a sample application zone of the substrate, which may be present at either end of the substrate. To describe the method steps sufficiently, the substrate design is briefly described herein to generally correlate the method steps to the device components. Referring to FIG. 1, a device 10, in accordance with one embodiment, comprises a substrate 12, with a first end 11 and a second end 31. The substrate is also shown in FIG. 6. The device 10 further comprises an amplification reagent reservoir 24, a wash reagent reservoir 26, an amplification reagent wicking pad 28 and a wash reagent wicking pad 30.

The substrate 12 comprises a sample application zone 14, which may also be used as a sample lysis zone and/or nucleic acid stabilization zone. The substrate further comprises fuses 16, which restrain the sample to be located at the sample application zone 14. The substrate further comprises a detection zone 20, which is located at the opposite end of the sample application zone 14, and near to the second end 31 of the substrate. In one or more embodiments, the substrate further comprises an amplification zone heating unit 22 covering the whole longitudinal strip. The substrate optionally contains a heating unit at or near the sample application zone for drying the loaded sample.

The method comprises applying a sample comprising target nucleic acids to a sample application zone of a substrate; wherein the substrate is an elongated strip 12. The sample solution, amplification reagent or washing solution may be applied to the sample application zone 14. In some embodiments, the amplification reagent and wash solution may be added upstream of the sample application zone. Non-limiting examples of the term "applying" include, contacting or disposing a sample or an amplification reagent or a washing solution on the substrate using a tube, pipette, catheter, syringe, conduit, an automatic injector, or using any other applicable ways/tools. In some embodiments, the sample may be poured onto the substrate.

In some embodiments, the applied sample is allowed to dry. Drying may include activation of a heating element, which is underneath or adjacent to the sample application zone 14. As illustrated in FIG. 1, an optional heating unit 18 is located near the sample application zone 14. The heating units may include, but are not limited to, an electrical heater, a chemical heater, an electro-mechanical heater, a radiation based heat-pad such as IR radiation heat pad. The sample may be dried on the substrate to stabilize the sample for a longer period of time.

The sample applied to the substrate, may be a biological sample, which is procured from physiological or clinical biological sources that comprise nucleic acids. In some embodiments, the sample is nucleic acid, in some other embodiments, the sample is a media from DNA or RNA synthesis; mixtures of chemically or biochemically synthesized DNA or RNA, wherein the sample is applied directly to the substrate followed by amplification or separation.

The nucleic acid may be extracted from cells using cell-lysis when the sample includes cells or tissue. For example, when the sample is collected from blood, thin sliced tissue, tissue culture cells, bacterial cells, body fluids such as urine, sputum, semen, secretions comprising DNA and/or RNA, sample is treated with a lysis reagent after or before applying it to the substrate. As such, in these embodiments, the method typically further comprises contacting the sample with a lysis reagent.

The sample may be pre-treated prior to applying to the sample application zone 14 with an additional lysis reagent for lysing cells which are difficult to lyse. For example, cells of Mycobacterium tuberculosis, which have a complex cell-wall structure that is impermeable and difficult to lyse, may be pre-treated with a lysis reagent before applying to the substrate.

In some embodiments of the method, the sample itself comprises a lysis reagent. In some other embodiments, the lysis reagent is impregnated in the sample application zone 14 of the substrate. The cells are lysed when contacted with the lysis reagents to extract nucleic acids from the cells. An example of a method for preparing a sample solution comprising nucleic acids from a biological sample comprises the step of lysing the biological sample using a lysis reagent, wherein the lysis reagent comprises chaotropic substances and/or other reagents.

In one or more embodiments, the method further comprises flowing an amplification buffer through the sample application zone along the length of the substrate for washing the substrate before amplification. The movement of the flow across the length of the substrate is referred to herein as a "lateral flow".

The amplification buffer carries away the impurities from the sample solution because of different affinities of impurities and nucleic acids to the substrate, such as a porous quartz fiber filter, thereby eliminating the needs for instruments to generate the external driving force (e.g. centrifugation force and pressure) and personnel with specific skills and enabling isolation on site and in remote areas. It appears that by flowing the amplification buffer through the sample application zone to carry impurities away, the nucleic acids become sufficiently separated from other components in the sample solution.

The washing step results in removing the lysis reagents, and/or stabilizing reagents impregnated in the substrate, which may inhibit downstream applications, such as amplification. In some embodiments, the nucleic acid amplification reaction mixture washes one or more inhibitors present on the substrate. The inhibitors or contaminants may also result from cell lysis, such as cell-debris or other cellular organelle, which have inhibitory effect on downstream processes and are removed by washing. In some embodiments, the washing dissolves the fuses 16, which subsequently activates the amplification zone heating unit 22. The amplification reagent may flow through the length of the substrate upon either dissolving the fuses or upon removal of the fuses.

In some embodiments, the method further comprises flowing a washing buffer along the substrate. The term "washing buffer" may interchangeably be used herein as a wash buffer or washing reagent or wash reagent. Referring to FIG. 1, the wash reagent may be stored in a wash reagent reservoir 26, and the wash reagent is flowed from the reservoir 26 to the wash reagent wicking pad 30 through the sample application zone 14. The wicking force inherent from the porosity of the bibulous substrate, such as a quartz fiber filter itself acts as the driving force to enable the amplification buffers to flow along the quartz fiber filter and through the sample application zone. The wicking pads 28, 30 draw the amplification and the washing buffers to flow towards the wicking pad 28, 30 based on its strong wicking force.

In some embodiments, the wash reagent and the amplification buffer are the same, and may be stored in a single reservoir. The amplification buffer may comprise amplification reagents except an enzyme, such as polymerase. In these embodiments, the washing solution may be replaced by amplification buffer, which may eliminate the step of washing during nucleic acid separation by combining the two steps, such as washing and separation of nucleic acids into one. In these embodiments, the nucleic acids are washed by diffusion of amplification buffer over the substrate 12. The washing buffer or amplification reagent solution flows along the substrate 12 under the wicking force, wherein no external force is used, and carries away the impurities having a less affinity to the quartz fiber filter than nucleic acids.

The method further comprises flowing a nucleic acid amplification reagent across a length of the substrate through the sample application zone. The terms "amplification reagent" and "amplification reagent solution" are interchangeably used hereinafter. The amplification reagent comprises a mixture of dNTP's, oligomer (primer), enzyme(s) including polymerase and amplification buffer.

In some embodiments, the amplification buffer, comprising a mixture of dNTP's, oligomer (primer), buffer and salts, is added to the substrate to rehydrate the substrate. To start the amplification reaction, the enzyme is added to the substrate separately. In some embodiments, the amplification reaction mixture starts amplification in the presence of the amplification buffer when in contact with the target nucleic acids at the sample application zone, wherein the amplification reaction mixture contains the enzyme. In some embodiments, the amplification reagents comprising dNTP mixture, oligomers, and amplification buffer reagents may be impregnated in the substrate, which may be reconstituted using an aqueous buffer. In these embodiments, the DNA polymerase is added before starting the amplification reaction. The amplification reagents may also comprise modified nucleotides.

Referring to FIG. 1, the amplification reagent may be stored in an amplification reagent reservoir 24. On completion of washing, the fuses 16 are dissolved and the lateral flow of amplification reagent starts flowing from the amplification reagent reservoir 24 and passes through the sample application zone 14 and the detection zone 20 to the amplification reagent wicking pad 28. The wicking pad generates a wicking force which enables the lateral flow of amplification reagent to migrate towards the wicking pad 28, across the length of the substrate.

In one or more embodiments, the amplification reagent flows through the substrate to amplify the target nucleic acid to form a nucleic acid amplification product (amplicons). In these embodiments, the target nucleic acid having a first molecular weight is substantially immobilized at the sample application zone 14 and the amplification product having a second molecular weight migrates away from the sample application zone. The amplification products may migrate via lateral flow. As noted, the terms "first", "second", and the like, as used herein do not denote any order, quantity, or importance, but rather are used to distinguish one element from another.

The nucleic acids having a first molecular weight may be substantially positioned around the sample application zone 14. The nucleic acids having a second molecular weight are substantially positioned around the detection zone 20. The term "substantially" used herein refers to a quantity of nucleic acids having certain molecular weights and positioned around the positioning portion, which may be at least about 15% of the total amount of nucleic acids having the molecular weights in the sample solution retains at the particular position, at least 50% of the total amount of nucleic acids having the molecular weights in the sample solution retains at the particular position, or at least 90% of the total amount of nucleic acids having the molecular weights in the sample solution retains at the particular position. For example, substantially the nucleic acids with first molecular weight means 90% of the total target nucleic acids applied to the substrate retains at the substrate at or around the sample application zone 14, and for nucleic acids with second molecular weight, 90% of the total amplified nucleic acids generated on the substrate retains at the substrate at or around the length of the substrate or, specifically, at or around the detection zone.

In some embodiments of methods, the amplification begins as the amplification reagents enter the sample application zone 14. In some embodiments, the amplification reaction starts when impregnated amplification reagents are rehydrated to reconstitute the reagents and nucleic acid polymerase added to the substrate. The amplification reagent may continue to flow through the detection zone 20 to the wicking pad 28. The amplification products may be captured in the detection zone 20 by one or more capturing agent or probe, such as primers. In some embodiments, the methods provide a continuous flow of amplification reagents and the amplification products through the detection zone. The amplification reagent may move from the reservoir to the wicking pad via a lateral flow, without forming a bolus.

In some embodiments, the method comprises flowing the nucleic acid amplification reaction mixture which separates the target nucleic acids and the amplification product according to their molecular weights. The target nucleic acids have first molecular weight and the amplified nucleic acids have second molecular weight, wherein the difference between the molecular weight may enable the amplified nucleic acids to be separated from the target nucleic acids during lateral flow. As can be seen from the examples, after diffusion of the amplification reagents through the sample application zone 14 along the length of the substrate 12, nucleic acids are positioned on the quartz fiber filter 12 according to the molecular weights thereof. To be specific, nucleic acids having higher molecular weights are positioned closer to the sample application zone 14 than nucleic acids having lower molecular weights.

The sample application zone 14 is the positioning portion for the nucleic acids having the first molecular weight. A substantial portion of the nucleic acids having a first molecular weight are positioned around the sample application zone 14. In some embodiments, the first molecular weight is in a range of at least about 50 kb. In some embodiments, the first molecular weight is in a range from about 50 kb to about 150 kb. In some embodiments, about 50 kb refers to a range of 50 kb±15 kb.

In some embodiments, substantial portion of the nucleic acids having a second molecular weight are positioned around the second end 31. In this case, the second end 31 is the positioning portion for the nucleic acids having the second molecular weight. The second molecular weight nucleic acids may be distributed across the substrate. In some embodiments, the second molecular weight is in a range of less than about 50 kb. In some embodiments, the amplicons may have more than one molecular weight population, which may results from more than one target molecules.

In some embodiments of the method, one or more amplification reactions occur on the substrate. In some embodiments, a first amplification reaction occurs at the sample application zone to generate a first amplification product. One or more amplification reactions may occur during migration of the first amplification product. Similarly, one or more amplification reactions may occur during migration of the second amplification product, and so on. Multiple amplification reactions generate plurality of amplification products, which facilitates detection method with greater ease, sensitivity and accuracy. Especially, the multiple amplification reactions are useful when the target nucleic acid is available in a trace quantity, for example, sample procured for forensic application or from biopsy sample.

In some embodiments, the amplification is an isothermal amplification reaction. The isothermal amplification may include but is not limited to, rolling circle amplification (RCA), multiple displacement amplification (MDA), helicase dependent amplification (HDA), ping pong amplification, cross priming amplification (CPA), recombinase polymerase amplification (RPA), loop mediated isothermal amplification (LAMP) and strand displacement amplification (SDA).

The amplified nucleic acids or amplicons may be detected on the substrate. In some embodiments, either the substrate comprises detection probes or the detection probes may separately be added during, prior or on completion of the amplification reaction. In some embodiments, a solution comprising one or more detection probes is added to the substrate. In some other embodiments, the detection probes are part of the amplification reaction mixture. A solution comprising one or more detection probes or an amplification reaction mixture comprising one or more detection probes may be flowed along the length of the substrate. In some embodiments, the detection probes may directly be added to the detection zone 20. In some examples, the detection probes in a form of solution or as a part of an amplification reaction mixture is applied at the detection zone 20.

The capturing probes may capture the amplified nucleic acids of interest on the substrate during diffusion of the probes. The term "capture" may include but are not limited to hybridization of the amplified nucleic acids with the probes, physical interaction of the probes with the amplified nucleic acids, or chemical interaction of the probes with the amplified nucleic acids. The amplification product may be immobilized on the substrate by a physical interaction with the substrate, using a capturing probe, using a detection probe or combinations thereof. In some embodiments, the amplification product is captured on the substrate by binding with a capturing probe physically bound to the substrate to form captured amplification product. The nucleic acids may be captured by the capture probe by hybridization, for example, when the capture probe is a primer. The captured amplification product may further bind to a detection probe for detection of amplicons.

The "detection probe" may detect the amplicons using one or more detection method. The detection probes may include, but are not limited to, antisense oligomer, pyrophosphate, phosphatase, biotin-streptavidin beads, antibody, fluorescence resonance energy transfer (FRET) probes, horseradish peroxidase (HRP) probes and luciferase. The antisense oligomers may comprise of natural nucleotides or nucleotide analogs. The oligonucleotides may be labeled with FRET probes, such as fluorescein, Cy5, Cy5.5, and BIODPY®.

The separated nucleic acids may be detected by various procedures. In some embodiments, the nucleic acids such as DNA may be detected by southern blot and RNA may be detected by northern blot. The nucleic acids are separated at the detection zone, may be detected by colorimetric detection method, chemical, electrical, pH, luminescent or fluorescence based detection method.

In some embodiments, the detection probe is an antisense oligomer which hybridizes with the amplified nucleic acids, wherein the antisense oligomer probe is attached to a molecular marker which can be detected. The molecular marker may include but is not limited to, radioactive molecules, fluorescent molecules, proteins or peptides. For example, a radioactive isotope of phosphorus $^{32}P$ is inserted in the phosphodiester linkage of the antisense oligomer, which may function as a detection probe. The detection probe may be tagged with a non-radioactive marker, such as digoxygenin. In this case, anti-digoxygenin antibody may be used to detect the digoxygenin labelled probe. In some examples, the detection probe is a chemical entity, which in contact with a moiety attached to the amplified nucleic acids may generate fluorescence signal. The detection probe may be an enzyme, which on interaction with a moiety on the amplified nucleic acids may produce a chemical which generates a color. This may distinguish the colored amplified product from the colorless target nucleic acids.

In some embodiments, the method further comprises: flowing a solution comprising primary detection probes through the sample application zone along the length of the substrate to bind to the captured amplification product to form a primary detection probe bound amplification product. Some embodiments of the method further comprises: flowing a solution comprising secondary detection probes through the sample application zone along the length of the substrate to bind to the primary detection probe bound amplification product. In some embodiments, the primary detection probe may be attached to a fluorescence moiety, wherein the secondary detection probe may be selected as a quencher. The secondary detection probe may quench the fluorescence generated by the primary detection probe on interaction. In some other embodiments, the primary detection probe may be attached to a primary antibody, wherein the secondary detection probe may be selected as a secondary antibody, wherein the secondary antibody may bind to the primary antibody and generate a signal.

In some embodiments, after extraction and separation of the nucleic acids, such as DNA and/or RNA, the nucleic acids may be stabilized for extended storage, depending on its application and requirement. The amplification product may be physically bound to the substrate, wherein the binding efficiency may be further increased using various reagents. In case of stabilization, the stabilizing reagents may be impregnated in the substrate. In some embodiments, the stabilizing reagents may be impregnated at the sample application zone 14, sample detection zone 20 or in the entire substrate 12. The stabilization reagents are described in more detail in later part of the specification.

In some embodiments, the method further comprises applying a flow barrier to the substrate to immobilize the amplification products by obstructing the amplification product flow. The fuses 16 may also be referred to herein as flow barriers. The amplification product may not flow further until the barrier is removed. The flow barrier may be a transverse section, disposed on the longitudinal strip of the substrate 12. The shape of the flow barrier may be any regular shape such as rectangular, square planar, spherical shape or any irregular shape. The flow barrier may be made of polymer, glass, wood, metal or combinations thereof. In some embodiments, the flow barrier comprises quartz, paper, sugar, salts or combinations thereof. In some embodiments, the flow barrier is located adjacent to the substrate 12 and after diffusion of the amplification buffer through the sample application zone 14 along the length of the substrate 12, a substantial portion of the nucleic acids are positioned at the interface between the sample application zone 14 and the flow bather. In some embodiments, the flow bather 16 is an elongated strip made of a material other than quartz fiber filter. In some embodiments, the flow barrier is made of cellulose, such as commercially available cellulose, for example, 31ETF (Whatman®).

In one or more embodiments of the method, a migration modifier is added to the substrate. In some embodiments, the sample application zone further comprises a migration modifier. The migration modifier may be used to modify the migration rate or pattern of the amplification product through lateral flow. The migration modifier may decrease the migration rate of one or more target molecules by ensuring better binding of the target nucleic acids to the substrate. The migration modifier modifies binding efficiency of the molecules to the substrate. Use of migration modifier ensures efficient separation and detection of the amplified product.

In some embodiments, the migration modifier comprises a chaotrope. The migration modifier may comprise a guanidinium salt, which may minimize the migration of the target DNA during the lateral flow of the amplified product DNA. In one embodiment, the migration modifier comprises guanidinium thiocyanate. Generally, guanidinium thiocyanate improves binding of genomic DNA to the substrate, which retains the target nucleic acid, such as genomic DNA bound at the sample application zone.

In some embodiments, the method further comprises providing a wicking pad adjacent to the second end 31 of the substrate, which may function as a stopping pad or collection pad. The stopping pad may stop the flow of amplified nucleic acids near the second end. The stopping pad may be substituted by a flow bather. The collection pad may collect the nucleic acids from the substrate by transferring the amplicons to the collection pad.

In some embodiments, the method further comprises adding a collection pad. In these embodiments, after diffusion of the washing buffer through the sample application zone 14 along the length of quartz fiber filter 12, the collection pad (a stopping pad, a wicking pad, or a quartz fiber filter) is disconnected from the substrate and replaced with a new collection pad so that the amplification buffer flows from the substrate to the new collection pad.

The amplification reagents or amplification buffer flows along the length of the quartz fiber filter and through the sample application zone to migrate nucleic acids on the quartz fiber filter, the lower the molecular weight, the further nucleic acids migrate on the quartz fiber filter from the sample application zone. When the amplification or wash buffer flows from the quartz fiber filter to a stopping or wicking pad made of a material other than the quartz fiber filter, nucleic acids migrating with the aqueous buffer will stop and be positioned at an interface between the quartz fiber filter and the stopping or wicking pad.

One or more embodiments of a substrate comprise a sample application zone for applying a sample comprising a target nucleic acid having a first molecular weight and flowing an amplification reaction mixture along the length of the substrate through the sample application zone forming a nucleic acid amplification product having a second molecular weight, and a detection zone for separating the nucleic acid amplification product having second molecular weight from the target nucleic acids having first molecular weight according to molecular weights of the amplified nucleic acids and target nucleic acids.

In some embodiments, the substrate is a solid substrate, which is a non-water dissolvable material, which enables collection, extraction, separation, detection and storage of nucleic acids followed by elution without solubilizing the material using water or aqueous buffer.

In some embodiments, the substrate is an elongated strip comprising a first end 11, a sample application zone 14, and a second end 31. The run time starting from sample application to separation may increase with increasing the length of the substrate, however the separation of the nucleic acids are better with increasing the length of the substrate. The length of the substrate may be optimized considering better separation as well as run time. The substrate may have a length in a range between 1 cm and 20 cm. In some embodiments, the substrate has a length less than 10 cm.

The substrate includes, but is not limited to, materials such as cellulose, cellulose acetate, nitrocellulose, glass fibers or combinations thereof. In one embodiment, the substrate comprises cellulose. In one or more embodiments, the substrate is selected from a nitrocellulose membrane, a cellulose membrane, a cellulose acetate membrane, a regenerated cellulose membrane, a nitrocellulose mixed ester membranes, a polyethersulfone membrane, a nylon membrane, a polyolefin membrane, a polyester membrane, a polycarbonate membrane, a polypropylene membrane, a polyvinylidene difluoride membrane, a polyethylene membrane, a polystyrene membrane, a polyurethane membrane, a polyphenylene oxide membrane, a poly(tetrafluoroethylene-co-hexafluoropropylene) membrane, and any combination of two or more of the above membranes. In some embodiments, the substrate comprises modified cellulose, such as pegylated cellulose or pegylated nitro cellulose.

In some embodiments, the substrate is a porous substrate. In one embodiment, the substrate is a porous cellulose membrane. In one embodiment, the solid substrate is a porous cellulose paper, such as a cellulose substrate from GE Healthcare Life Sciences (formerly Whatman™). In one example, the cellulose substrate comprises 903-cellulose, FTA™ or FTA™ Elute.

The sample solution comprising nucleic acids is applied to the sample application zone 14 of the quartz fiber filter 12. The sample application zone 14 may be in any shape or configuration that the sample solution may be applied thereto. In some embodiments, the sample application zone 14 of the quartz fiber filter 12 comprises a lysis reagent and the biological sample comprising nucleic acids is directly applied to the sample application zone 14 of the quartz fiber filter 12. In one or more embodiments of the device, the sample application zone comprises an FTA pad.

In one or more embodiments, the substrate comprises one or more cell-lysis reagents, protein denaturing agents or stabilizing agents in a substantially dry state. In other embodiments, the substrate further comprises buffer reagents, reducing agents, and optionally free-radical scavengers in addition to protein denaturing agents in a dry state. The substrate may extract nucleic acids and preserve nucleic acids under dry conditions, wherein the dried nucleic acids may further be eluted from the substrate by re-hydrating with water or aqueous buffer.

As noted, the sample application zone comprises a lysis reagent, wherein the lysis reagent may comprise chaotropes. The examples of chaotropic substances include, but are not limited to, guanidinium hydrochloride, guanidinium chloride, guanidinium isothiocyanate/thiocyanate, sodium thiocyanate, sodium perchlorate, sodium iodide, potassium iodide, urea, and/or any combination thereof. A typical anionic chaotropic series, shown in order of decreasing chaotropic strength, includes: $CCl_3COO^-$, $CNS^-$, $CF_3COO^-$, $ClO_4^-$, $I^-$, $CH_3COO^-$, $Br^-$, $Cl^-$, or $CHO_2^-$. The lysis reagent may include chaotropic substances in concentrations of from 0.1 M to 10 M, or from 1 M to 10 M.

For some of the biological samples, such as bacteria, the lysis reagent may comprise, for example, lytic enzymes or the biological samples may be pretreated, for example, with lytic enzymes, prior to being lysed.

In some embodiments, the lysis reagent also includes a sufficient amount of buffer. The examples of buffers for use in the lysis reagent include tris-(hydroxymethyl) aminomethane hydrochloride (Tris-HCl), sodium phosphate, sodium acetate, sodium tetraborate-boric acid and glycine-sodium hydroxide.

In some embodiments, the lysis reagent also includes a non-ionic surfactant, a cationic surfactant, an anionic surfactant, an amphoteric surfactant, and/or any combination thereof. Exemplary nonionic surfactants include, but are not limited to, t-octylphenoxypolyethoxyethanol (TRITON X-100™), (octylphenoxy)polyethoxyethanol (IGEPAL™ CA-630/NP-40), triethyleneglycol monolauryl ether (BRIJ™ 30), sorbitari monolaurate (SPAN™ 20), or the polysorbate family of chemicals, such as polysorbate 20 (i.e., TWEEN™ 20), TWEEN™ 40, TWEEN™ 60 and TWEEN™ 80 (Sigma-Aldrich, St. Louis, Mo.). Examples of cationic surfactants include cetyltrimethylammonium bromide, dodecyltrimethylammonium chloride, tetradecyltrimethylammonium chloride and cetylpyridinium chloride.

The concentration of the surfactant in the lysis reagent could vary slightly among the different surfactants and depending on the components in the biological sample to be lysed. In some embodiments, the concentration of the surfactant is in a range of from about 0.01% to about 20% by weight. The lysis reagent may further comprise dithiothreitol (DTT).

The lysis reagent may also comprise protease, such as serine, cystine and metallic proteases. A protease free of nuclease may be used. A protease comprising a stabilizer, such as metallic ions, may be used. The protease may be used, upon addition, in an amount of preferably from about 0.001 IU to about 10 IU, more preferably from about 0.01 IU to about 1 IU, per ml of the whole lysis reagent.

The lysis reagent may comprise a defoaming agent. Examples of the defoaming agent include silicon-comprising defoaming agents (e.g., silicone oil, dimethylpolysiloxane, silicone emulsion, modified polysiloxane and silicone compound), alcohol series defoaming agents (e.g., acetylene glycol, heptanol, ethylhexanol, higher alcohol and polyoxyalkylene glycol), ether series defoaming agents (e.g., heptyl cellosolve and nonyl cellosolve-3-heptylsorbitol), fat-and-oil series defoaming agents (e.g., animal oils and plant oils), fatty acid series defoaming agents (e.g., stearic acid, oleic acid and palmitic acid), metallic soap series defoaming agents (e.g., aluminum stearate and calcium stearate), fatty acid ester series defoaming agents (e.g., natural wax and tributyl phosphate), phosphate series defoaming agents (e.g., sodium octylphosphate), amine series defoaming agents (e.g., diamylamine), amide series defoaming agents (e.g., stearic acid amide), other defoaming agents (e.g., ferric sulfate and bauxite), and any combination thereof.

The lysis reagent may comprise an alcohol. Any of a primary alcohol, a secondary alcohol and a tertiary alcohol may be used. Methyl alcohol, ethyl alcohol, propyl alcohol, butyl alcohol, and an isomer thereof may preferably be used. The concentration of alcohol in the lysis reagent is preferably in a range of from about 5% to about 90% by weight.

In some embodiments, the lysis reagent is RA1 lysis buffer from Illustra RNAspin Mini kit (cat#25-0500-71) supplemented with 0.35 µl 2-beta-mercaptoethanol (BME, cat#60-24-2).

The method for preparing the sample solution comprising nucleic acids may be conducted with the aid of, for example, a ultrasonic wave treatment, a treatment using a sharp projection, or a high-speed stirring or vortexing treatment.

In one embodiment, the substrate is impregnated with nucleic acid stabilizing reagents. These stabilizing reagents may include DNA-decomposing enzyme inhibitor, such as DNAse inhibitor and/or RNA-decomposing enzyme inhibitor, such as RNAse inhibitor, buffer reagents, or chelating agents (e.g., EDTA).

As noted, the substrate comprises an RNase inhibitor, wherein the RNase inhibitor comprises vanadyl ribonucleoside complex (VRC), a nucleotide analogue, a commercially available RNase inhibitor (e.g., SUPERase-In™), or a triphosphate salts, such as sodium triphosphate.

The substrate may comprise DNAse inhibitor, which may include but is not limited to, 2-mercaptoethanol, 2-nitro-5-thiocyanobenzoic acid, Actin, Alfatoxin B2a, G2, G2a, and M1, $Ca^{2+}$, EGTA, EDTA, Sodium dodecyl sulfate, Calf spleen inhibitor protein, Carbodiimide and cholesterol sulfate, Iodoacetate.

In some embodiments, the substrate comprises stabilizing reagent, which may include a reducing agent that facilitates denaturation of RNase and aids in the isolation of undegraded RNA. Exemplary reducing agent includes, but is not limited to, 2-aminoethanethiol, tris-carboxyethylphosphine (TCEP), and β-mercaptoethanol.

As noted, the substrate further comprises a chelating agent, wherein the chelating agent is selected from ethylenediaminetetraacetic acid (EDTA), citric acid, ethylene glycol tetraacetic acid (EGTA) or combinations thereof.

The substrate may further comprise a UV protectant, a free-radical scavenger, a chelator or combinations thereof for stabilizing nucleic acids. Without intending to be limited to any specific UV protect, an exemplary antioxidants include, for example, hydroquinone monomethyl ether (MEHQ), hydroquinone (HQ), toluhydroquinone (THQ), uric acid, and ascorbic acid. In some embodiments, the antioxidant is THQ.

As noted, in some embodiments, the substrate comprises one or more detection probes. The detection probes may be located at the sample application zone, downstream of the sample application zone or combinations thereof. In one embodiment, one or more detection probes are located on the substrate 12, downstream 20 of the sample application zone 14.

The detection probes may be impregnated in the substrate. In some embodiments, the detection probes are impregnated in the substrate under dried condition, wherein the impregnated detection probes may be rehydrated during the process of amplification or after the amplification reaction is over. The impregnated detection probes may be reconstituted and activated by rehydration.

In one embodiment, the device comprises a substrate and an amplification reagent reservoir. In some embodiments, the device further comprises a wash reagent reservoir.

Referring to FIG. 1, the device 10 comprises a substrate 12 having a first end 11 and a second end 31. In some embodiments, the substrate is an elongated strip. The device 10 further comprises an amplification reagent reservoir 24, a wash reagent reservoir 26, an amplification reagent wicking pad 28 and a wash reagent wicking pad 30. In some embodiments, the substrate 12 either directly or indirectly coupled to the amplification reagent reservoir 24, wash reagent reservoir 26, and the wicking pads 28 and 30. In an embodiment of the device, the amplification reagent reservoir 24, sample application zone 14 and amplification reagent wicking pad 28 are on a first straight line, and the wash reagent reservoir 26 and the wash reagent wicking pad 30 are present on a second straight line which is perpendicular to the first straight line. Any other arrangement that maintains similar connectivity of different components of the device may also be possible. Although the term "coupled" refers to connected and often is used to describe physical or mechanical connections or couplings, the term is not intended to be so restricted and can include direct or indirect connections or couplings.

The substrate 12 comprises a sample application zone 14. The sample application zone 14 may also be used as a sample lysis zone and/or nucleic acid stabilization zone. The substrate further comprises fuses 16, which retain the sample at the sample application zone, and do not allow the sample to flow outside of the boundary formed by the fuses 16. The substrate further comprises a detection zone 20, which comprises a control line and a test line. The detection zone 20 is located at the opposite end of the sample application zone 14 of the longitudinal strip 12. In one or more embodiments, the substrate further comprises an amplification zone heating unit 22 covering the whole longitudinal strip. The amplification zone heating unit may require maintaining an isothermal condition for amplification reaction. In some embodiments, the substrate optionally contains a heating unit for drying the loaded sample 18. In some embodiments, the substrate 12 is made of quartz fiber filter.

In one embodiment, a device 10 comprises an elongated strip of quartz fiber filter 12. The quartz fiber filter 12 includes a first end comprising a sample application zone 14 and a detection zone 20 at a second end opposite to the first end 14.

The device comprises one or more wicking pads. The wicking pad may be a porous matrix. In some embodiments, the porous matrix may be bibulous, to which the sample solution comprising nucleic acids is sorbed efficiently. The bibulous porous matrix does not inhibit storage or subsequent analysis of the nucleic acid applied thereto. In some embodiments, the wicking pad is a quartz fiber filter. The quartz fiber filter may be made of pure quartz fibers with no binders. In some embodiments, the quartz fiber filter has a particle retention efficiency of about 98% for particles of a size of no less than 2.2 µm, a basis weight of 85 g/m², and a thickness in a range of from about 300 µm to about 600 µm. Examples of quartz fiber filters suitable for this purpose include, but are not limited to, Whatman® grade QM-A quartz microfiber filters available from GE Healthcare Bio-Sciences Corp., (New Jersey, USA), and AQFA quartz fiber filters available from Millipore Corporation (Billerica, Mass., USA). The wicking pad may be a strip of bibulous material, such as cellulose, silica microfiber filter or glass fiber. In some embodiments, the wicking pad 28, 30 is Whatman® grade 470 special purpose filter papers commercially available from GE Healthcare, New Jersey, USA.

Figure 2:
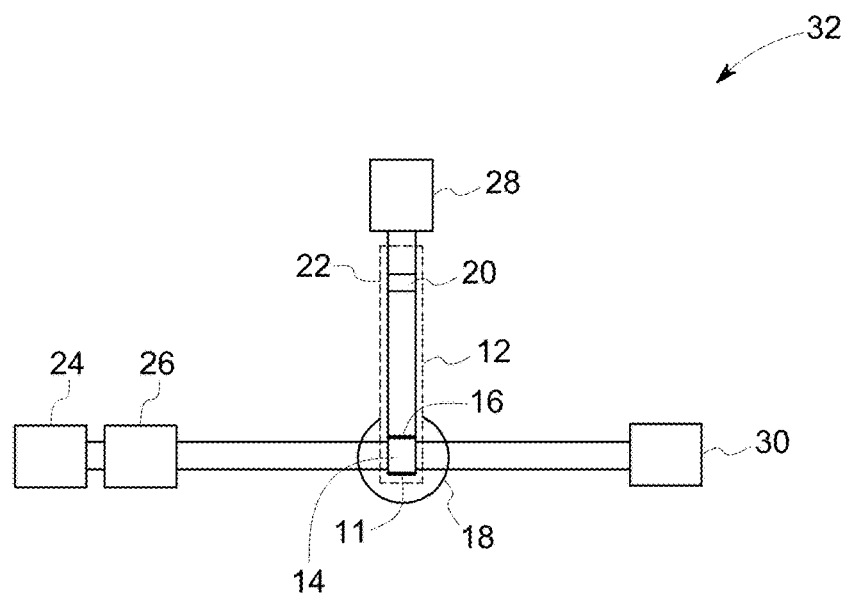
FIG. 2 illustrates a schematic diagram of a device in accordance with another example of an embodiment of the invention.

FIG. 2 illustrates another embodiment of a device 32, wherein the device is similar to the device described in FIG. 1, except the fact that, the amplification reagent reservoir 24 and the wash reagent reservoir 26 are coupled to each other. In some embodiments, the amplification reagent reservoir 24 and the wash reagent reservoir 26 are adjacent to each other, configured such that the wash reagent reservoir is directly coupled to the substrate 12. The amplification reagent reservoir is indirectly coupled to the substrate 12, through the wash reagent reservoir 26. In this embodiment, both the amplification reagent reservoir 24 and the wash reagent reservoir 26 are aligned on a straight line with the sample application zone 14 and the wash reagent wicking pad 30. This configuration results in supplying the wash reagent first to the substrate 12, through the sample application zone 14 and extracted out the impurities or inhibitors, if present at the sample application zone, to the wicking pad 30. On completion of washing, the amplification reagents stored in the reservoir 24 starts migrating to the substrate 12 through the wash reagent reservoir 26. The amplification reaction starts when the amplification reagent comes in contact with the target nucleic acids at the sample application zone 14. The device comprises a heating unit 22 for amplification zone, which helps in maintaining a constant temperature for substrate during amplification reaction. The device may further comprise a sample heating unit 18 for drying the nucleic acids for stabilization.

Figure 3:
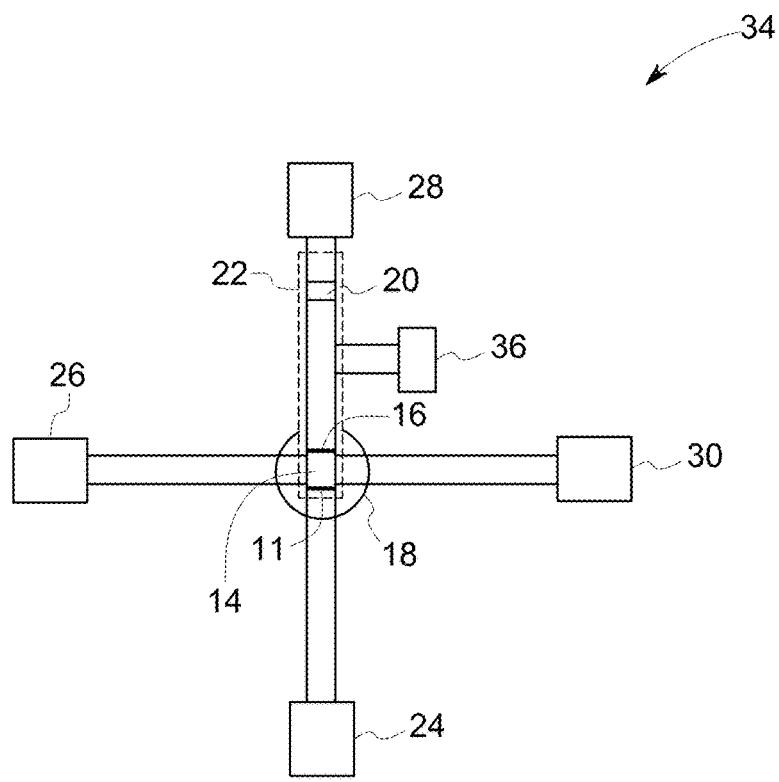
FIG. 3 illustrates a schematic diagram of a device in accordance with another example of an embodiment of the invention.

FIG. 3 illustrates another embodiment of a device 34, wherein the device is similar to the device described in FIG. 1, except the fact that, the device further comprises a wicking pad 36 near the sample application zone 14. The fuses 16 are disposed such that they form a boundary starting from sample application zone 14 and ending at wicking pad 36. In an embodiment of the device, the amplification reagent reservoir 24, sample application zone 14 and amplification reagent wicking pad 28 are on a first straight line, and the wash reagent reservoir 26 and the wash reagent wicking pad 30 are present on a second straight line which is perpendicular to the first straight line. Any other arrangement that maintain similar connectivity of different components of the device may also be possible. In this embodiment, the amplification reagent reservoir 24, the wash reagent reservoir 26, and the wicking pads 28 and 30 are directly coupled to the substrate 12. The wash reagent is first supplied to the substrate 12, through the sample application zone 14 and extracted out the impurities or inhibitors, if present at the sample application zone, to the wicking pad 30. On completion of washing, the amplification reagents stored in the reservoir 24 starts migrating to the substrate 12. The amplification reaction starts when the amplification reagent comes in contact with the target nucleic acids at the sample application zone 14. The device of this embodiment also comprises a heating unit 22 for amplification zone and a sample heating unit 18.

Figure 4:
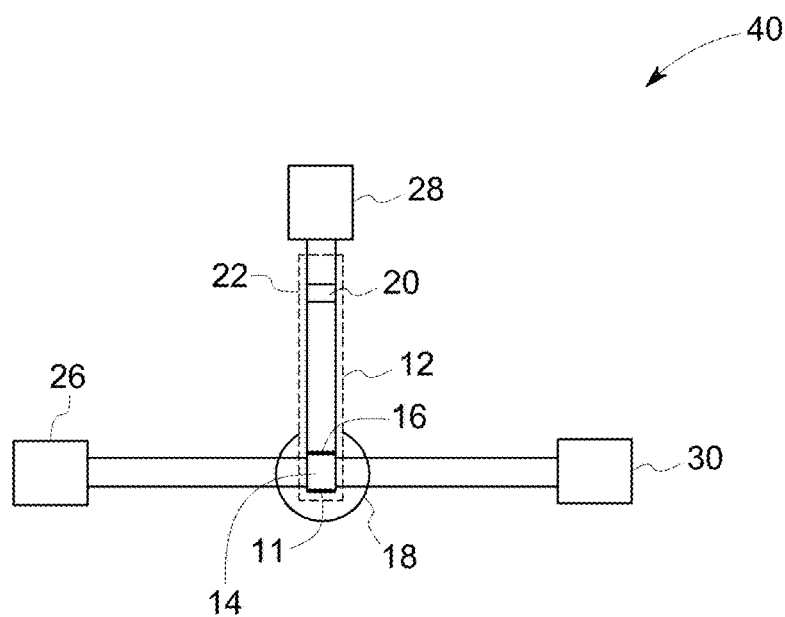
FIG. 4 illustrates a schematic diagram of a device in accordance with an example of an embodiment of the invention.

Referring to FIG. 4, which illustrates another embodiment of a device 32. The device of this embodiment is similar to the device described in FIG. 2, wherein the device of FIG. 4 comprises only one reservoir, such as amplification reagent reservoir 24 which comprises the amplification reagent, which is directly coupled to the substrate 12. The device does not specifically need to contain any washing reagent or a washing reagent reservoir. In these embodiments, the amplification reagent may function as the wash reagent. In this embodiment, the amplification reagent reservoir 24 is aligned on a straight line with the sample application zone 14 and the wash reagent wicking pad 30. In this embodiment, the amplification reagent flows to the substrate 12, through the sample application zone 14 and extracts out the impurities or inhibitors, if present at the sample application zone, and to the wicking pad 30. On completion of washing, the amplification reagents stored in the reservoir 24 further migrate to the substrate 12. The amplification reaction starts when the amplification reagent, comprising the enzyme, comes in contact with the target nucleic acids at the sample application zone 14. The amplification reagent serves as the wash reagent until the lysis reagent in the sample application pad (e.g., guanidinium thiocyanate) is sufficiently removed. The lysis reagent inhibits amplification, so once inhibitors are removed, the amplification reagent including the polymerase starts amplifying the nucleic acids. The device comprises a heating unit 22 for amplification zone, which helps in maintaining a constant temperature for substrate during amplification reaction. The device may further comprise a sample heating unit 18, for drying the nucleic acids for stabilization. In some embodiments, the heating unit supplies heat necessary for cell lysis.

Figures 5A, 5B:
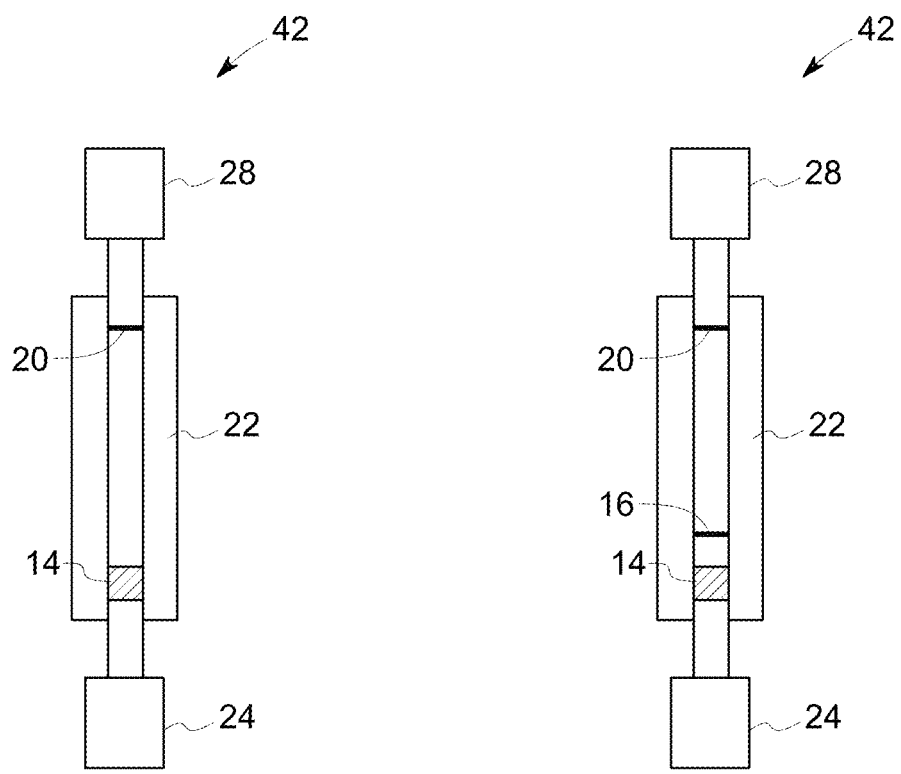
FIG. 5A illustrates a schematic diagram of a device in accordance with another example of an embodiment of the invention.
FIG. 5B illustrates a schematic diagram of a device in accordance with another example of an embodiment of the invention.
Figure 5D:
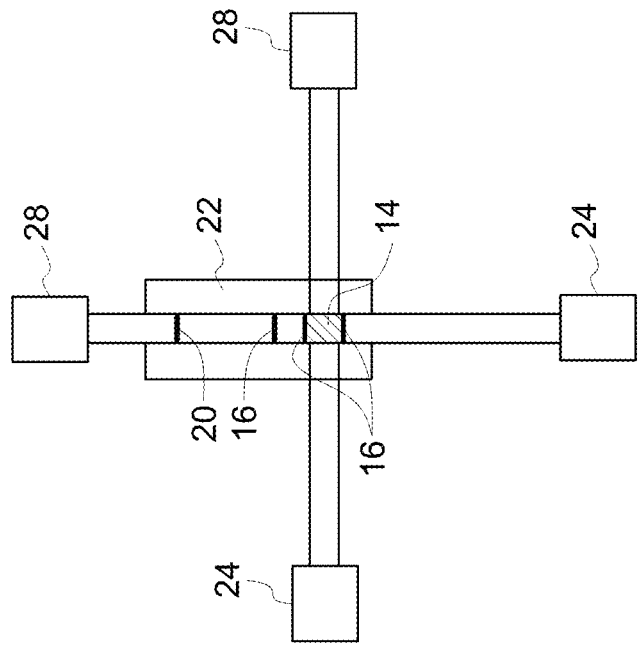
FIG. 5D illustrates a schematic diagram of a device in accordance with another example of an embodiment of the invention.
Figure 5C:
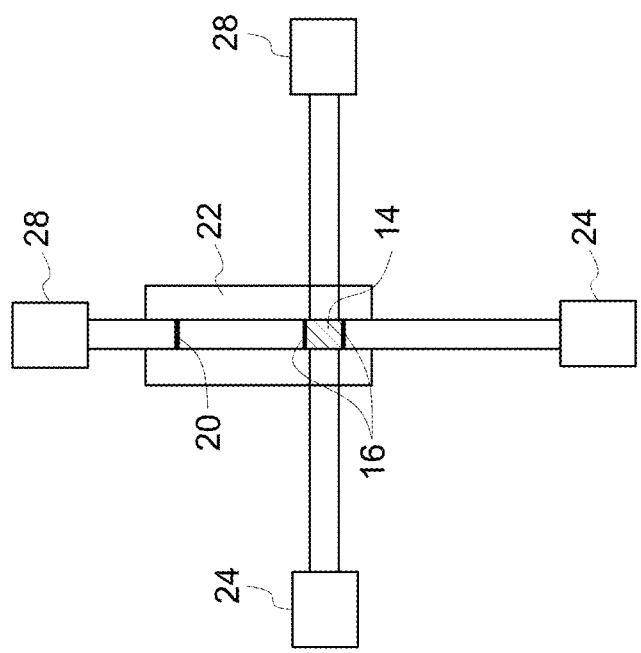
FIG. 5C illustrates a schematic diagram of a device in accordance with another example of an embodiment of the invention.

In addition to in-solution and in-paper lysis approaches, two classes of topologies may be used for amplification, such as (1) amplification during lateral flow or amplification-in-flow 42, 46, as shown in FIGS. 5A and 5C; and (2) amplification restricted in a defined place or amplification-in-place 44, 48, as shown in FIGS. 5B and 5D. Amplification-in-flow requires that the target nucleic acids, such as DNA have high molecular weight, wherein the amplification is initiated in the sample application zone. The low molecular weight amplicons that are generated may migrate downstream of the substrate, wherein that portion of the substrate has an amplification zone heating unit 22 and the amplicons continue to amplify further, yielding a semi-continuous delivery of amplicons to the detection line 20.

Alternatively, amplification in-place topologies use fuses, such as valves, gates, switches or fuses in the flow path to ensure that amplification occurs in a largely static fluid volume within the amplification zone comprising a heating unit 22. The amplicons are allowed to flow on to the detection zone only after the desired amplification time has elapsed by opening or closing of a valve or lapse of a delay circuit 16.

Some other embodiments of a device are illustrated in FIGS. 5A, 5B, 5C and 5D, wherein the device illustrates in flow and in-place topology which comprise an amplification reagent reservoir 24, a substrate 12 and a wicking pad 28. In an embodiment, the amplification reagent reservoir 24, the substrate 12 and the wicking pad 28 are located in a straight line. The substrate comprises a sample application zone 14, a detection zone 20 and a heating unit for amplification 22. The detection zone 20 comprises a test line. The test line is where the amplicons are captured for detection, for example, using colored beads hybridized to the captured amplicons for detection. The devices of FIGS. 5B, 5C and 5D additionally have one or more fuses 16. In the presence of a fuse, the amplification reaction mixture does not flow through the substrate. In the absence of fuse, the amplification reaction mixture flows through the substrate 12, followed by amplifying the target nucleic acids and separating the nucleic acids based on molecular weight in the detection zone 20.

The quartz fiber filter, the collection pad, the wicking pad, the stopping pad may be supported on a backing material such as a plastic material like polyester (Mylar®) or polyethylene terephthalate (PET).

In some embodiments, the device 10, 32, 34, 40 or 42 comprises a plastic housing (not shown) enclosing the quartz fiber filter 12, the collection pad or amplification reagent wicking pad 28, the wicking pad 28, 30 the stopping pad therein but exposing the sample application zone 14 with corresponding opening thereof so that the sample solution comprising nucleic acids, the washing buffer, and the aqueous buffer may be applied to the sample application zone 14. In some embodiments, the sample application zone 14 may be located outside of the housing.

The device 10 may be a simple nucleic acid purification/isolation/separation device, or alternatively may be a part or components of a larger nucleic acid analysis device or system.

As noted, the residual lysis reagents, inhibitors or other impurities from the sample application zone 14 may be washed off before amplification and separation using the amplification buffer. In some embodiments, an additional washing solution may be used, wherein the washing solution comprises an aqueous buffer, which may be any solvent of nucleic acids. In some embodiments, the aqueous buffer comprises tris(hydroxymethyl)aminomethane, ethylenediaminetetraacetic acid (EDTA) buffer, phosphate buffered saline (PBS) or Tris EDTA (TE) in which the tris buffer is substituted with HEPES. As noted, the aqueous buffer flows through the sample application zone 14 along the length of quartz fiber filter 12. In some embodiments, the first end 11 of the substrate is placed into the aqueous buffer so that the aqueous buffer flows from the first end 11 of the substrate 12.

The washing buffer may comprise an enzyme capable of degrading a contaminant, e.g., protein. Moreover, it may comprise deoxyribonuclease, ribonuclease or the like depending on circumstances. Use of washing buffer comprising deoxyribonuclease allows selective recovery of RNA. Similarly, use of a ribonuclease-comprising washing buffer allows selective recovery of DNA.

The amplification buffer may comprise a water-soluble organic solvent and/or water-soluble salt. The washing buffer washes out an impurity in a sample solution, which is adsorbed on the quartz fiber filter together with nucleic acids. Therefore, it may have a composition which desorbs the impurity from the quartz fiber filter while keeping nucleic acids adsorbed. A water-soluble organic solvent, e.g., alcohol, in which nucleic acids are sparingly soluble, is suitable for desorbing components other than nucleic acid from the quartz fiber filter. At the same time, incorporation of a water-soluble salt enhances the effect of adsorbing nucleic acids to improve selective desorption of an unnecessary component.

The water-soluble organic solvents may be used as a washing buffer include, but are not limited to, methanol, ethanol, isopropanol, n-propanol, butanol and acetone. The water-soluble organic solvent is incorporated in a washing buffer preferably at about 20% to about 100% by weight, more preferably about 40% to about 100% by weight. In one embodiment, an exemplary water-soluble salt to be included in a washing buffer is preferably a halide salt or tris (hydroxymethyl)aminomethane.

The amplification buffer for washing the substrate may be applied to the quartz fiber filter at the same place as where the sample solution comprising nucleic acids is applied, i.e., the sample application zone. The amplification buffer may also be applied to the quartz fiber filter at a place different from both the sample application zone and the buffer loading portion.

In some embodiments, the amplification buffer flows to the second end 31 (FIG. 6) and carries unwanted contaminants in the sample solution to the second end. The second end 31 is then cut off before flowing the amplification reagents or amplification buffer. In such way, the nucleic acids positioned on the remaining quartz fiber filter are purified/separated/isolated from the unwanted contaminants.

After diffusion of the amplification buffer, the nucleic acids positioned on the quartz fiber filter may be eluted under conditions of low ionic strength or with water, respectively.

As used herein, the term "sorb" means that the sample solution is absorbed, adsorbed or otherwise incorporated into or onto the sample application zone in such a way as not to be readily removed from the sample application zone unless subjected to conditions which are intentionally or inadvertently performed to remove the sorbed composition from the sample application zone.

The following examples are included to provide additional guidance to those of ordinary skill in the art in practicing the claimed invention. These examples do not limit the invention as defined in the appended claims.

EXAMPLES

Example 1

Preparation of GF/F Substrate

Figure 7A:
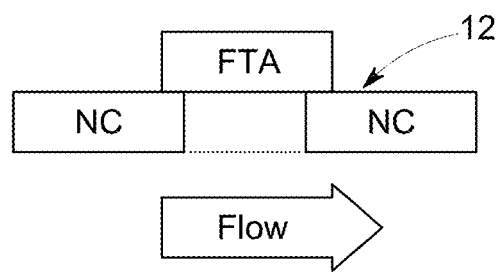
FIG. 7A illustrates side view of a schematic diagram of an example of a nitrocellulose substrate (NC) and a sample application zone (FTA) on the substrate in accordance with one embodiment of the invention.
Figure 7B:
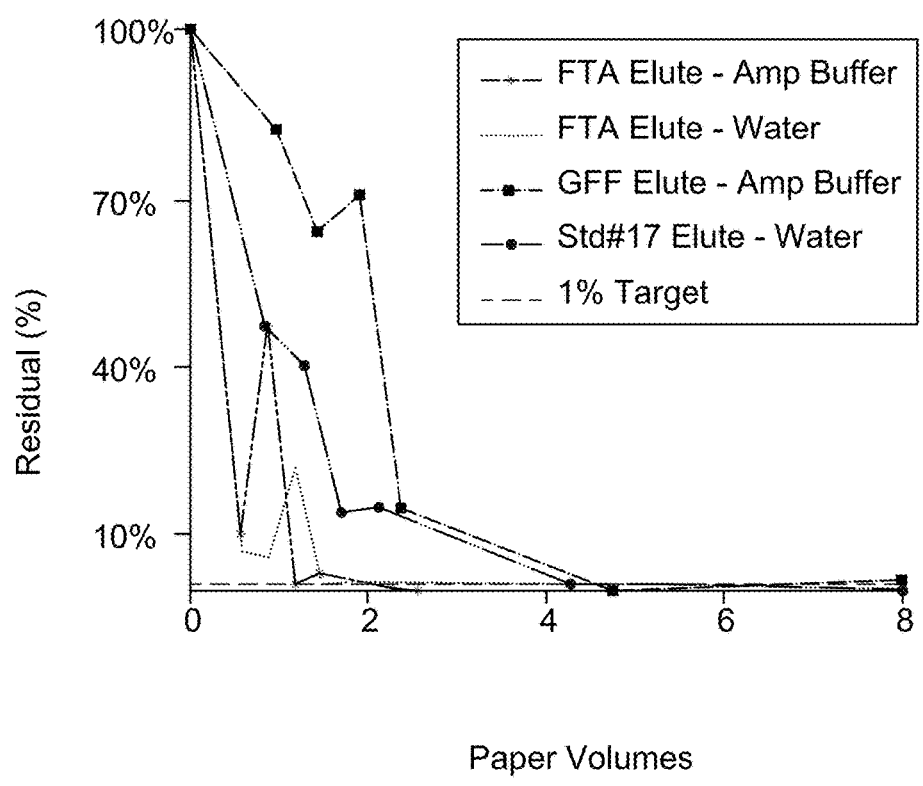
FIG. 7B illustrates an FTIR-ATR spectroscopy for different substrate composition to determine residual composition on washing.

A GF/F porous matrix (Whatman®-GE Healthcare) was soaked in a solution of 280 mg/ml guanidinium thiocyanate (Sigma-Aldrich) and allowed to air dry. This treated matrix was then cut into 5×5 mm squares and each square assembled on a modified lateral flow strip using PDMS glue. Each lateral flow strip (substrate) 12 was modified by removing an area approximately 10-12 mm from the pointed tip 11 underneath where the 5 mm square of treated GF/F porous matrix 14 would reside, as shown in FIG. 6. One strip was processed with a wick 28 present on the end opposite the point 11 (FIG. 8), while the other strip was processed without a wick. The GF/F glass fiber comprised elute-chemistry that was bridging a gap in a nitrocellulose strip (as shown in FIGS. 6 and 7 A).

Example 2

Preparation of a Modified Porous Nitrocellulose Based Substrate

A modified porous matrix was prepared by soaking a nitrocellulose based substrate (GE Healthcare) in an aqueous solution containing 10% (w/v) polyethylene glycol methyl ether methacrylate 300 (PEG; Sigma-Aldrich) and 30% (v/v) Tween 20 (Sigma-Aldrich) for 10 seconds. Excess solution was removed and the treated matrix subjected to E-beam (Advanced Electron Beam) treatment for a total dose of 10 kGy. Following irradiation, the modified matrix was treated as follows: 1) washed by soaking three times for 30 minutes each in distilled water using an orbital rotating platform, 2) the excess water removed and 3) allowed to air dry at room temperature overnight.

Example 3

Cell Lysis Using Modified Substrate

The FTA® papers (GE Healthcare) were used to accelerate thermal lysis of a *Staphylococcus* test strain. Here, in addition to traditional cellulose based papers, FTA® chemistry was applied to glass fiber membranes (GF/F and Standard 17). A summary of the efficacy of these materials is shown in Table 1 for the two classes of materials demonstrating lysis at different temperature and time. Furthermore, to determine the effects of incomplete water loss during sample lysis, each FTA sample was placed in "sealed" (Kapton tape), "open," or partially-sealed "capped", (e.g. under a cap with a small headspace) configurations. As shown in Table 1, successful lysis (*S. chromogenes*) was achieved for all tested configurations (as shown by cross in Table 1), including sealed and capped configurations, indicating that complete drying is not a requisite for cell lysis. Generally, lower incubation temperatures require longer incubation time to ensure six-log reduction in viable bacterial load (*S. chromogenes*), even at 49° C. for isothermal DNA amplification. A complete lysis was achieved in 10 minutes under the above conditions with FTA Elute chemistry. Similar findings were observed in experiments with *S. aureus*, and thus 49° C. and 15 minutes (or less) were down-selected for initial integrated device demonstration to showcase the potential utility of FTA® solid substrate lysis.

TABLE 1

| Substrate | Mode | Time (min) at 90° C. | | | | Time (min) at 49° C. | | |
|---|---|---|---|---|---|---|---|---|
| | | 1 | 2 | 5 | 10 | 10 | 15 | 20 |
| FTA Elute | Open | | X | | | X | | |
| (Cellulose) | Capped | X | X | X | X | X | X | X |
| | Sealed | | X | X | X | X | X | X |
| Glass | Open | | | | | X | X | |
| Fiber + | Capped | X | X | X | | X | X | |
| Elute | Sealed | X | X | X | | | | |

Example 4

Substrate Selection for Amplification

To evaluate FTA® Elute chemistry compatibility with amplification, punches (5 mm×5 mm) were placed on a nitrocellulose (NC) strip with a gap (to ensure flow through the paper) and washed with various volumes, as shown in FIG. 7 A. After the fluid in the well was exhausted, the punch was removed from the strip to prevent backflow during drying. The punches were dried in air overnight and then characterized by FTIR-ATR spectroscopy (FIG. 7 B) to determine the degree of washing relative to an unwashed FTA® paper and to a sample of the base paper from which FTA® paper is produced.

Generally the expectation was that, the amplification would not be inhibited if the residual chemistry was reduced to <1% of its initial level. The FTIR-ATR data shown in FIG. 7 B, which illustrates that FTA® Elute, in cellulose and glass fiber, were both washed and reduced to <1% residual composition for 25-50 μl (2-5 paper volumes) depending on the paper material. These volumes would not be an excessive amount of fluid to pass through an integrated device for the purpose of removing FTA® chemistry from the FTA® papers. The following validate that the washed FTA® papers are able to support amplification.

Example 5

Lateral Flow Migration of High Molecular Weight DNA (≥50 kb) and Effect of Washing To examine the migration of the template DNA during the washing and amplification processes, approximately one million cells in a 10 μl volume ($10^6$ CFU) from an overnight culture of methicillin-sensitive *Staphylococcus aureus* (*S. aureus*; ATCC) or MSSA were applied to the treated GF/F square (step 1, 52 of FIG. 8) and were then heated at 49° C. for 10 minutes to lyse the cells. An amplification reaction buffer comprising various reactants was used for washing solution, wherein the amplification buffer is devoid of enzyme, such as polymerase.

Figure 8:
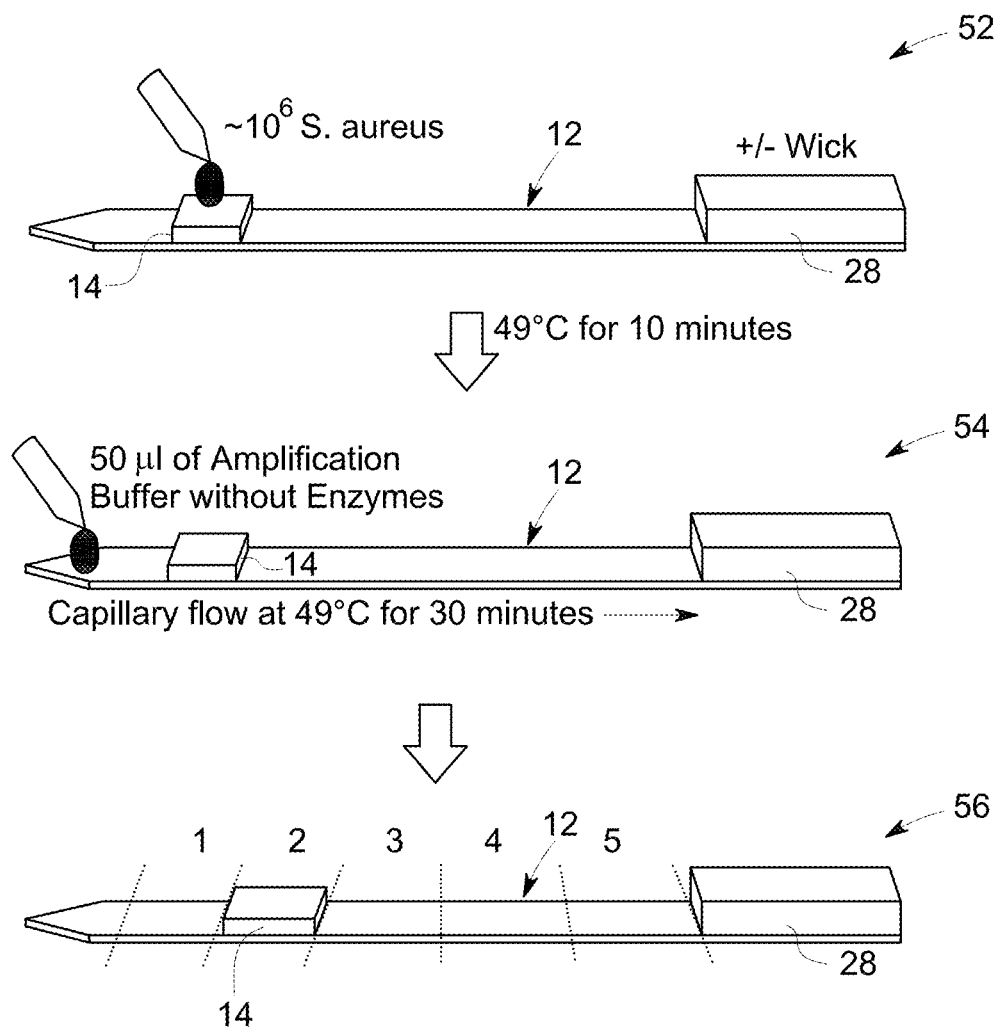
FIG. 8 is a flow diagram that illustrates sample application, washing and cutting the substrate in pieces for analyzing by gel electrophoresis.

Lateral flow was initiated 54 by placing amplification reaction mixture on the pointed tip of the strip (substrate) 12, as shown in step 2 (54) of FIG. 8. Subsequently amplification buffer (without enzymes) was allowed to flow through the strip. 25 μl of amplification reaction mixture were added to the strip 12 without a wicking pad, while 100 μl of amplification reaction mixture were added to the strip 12 with a wicking pad, wherein the amplification mixture did not include enzymes. Capillary flow was allowed to continue for 30 minutes at 49° C. Once capillary flow was terminated, each strip was sectioned into five equal portions as indicated in step 3 (56) of FIG. 8.

Figure 9:
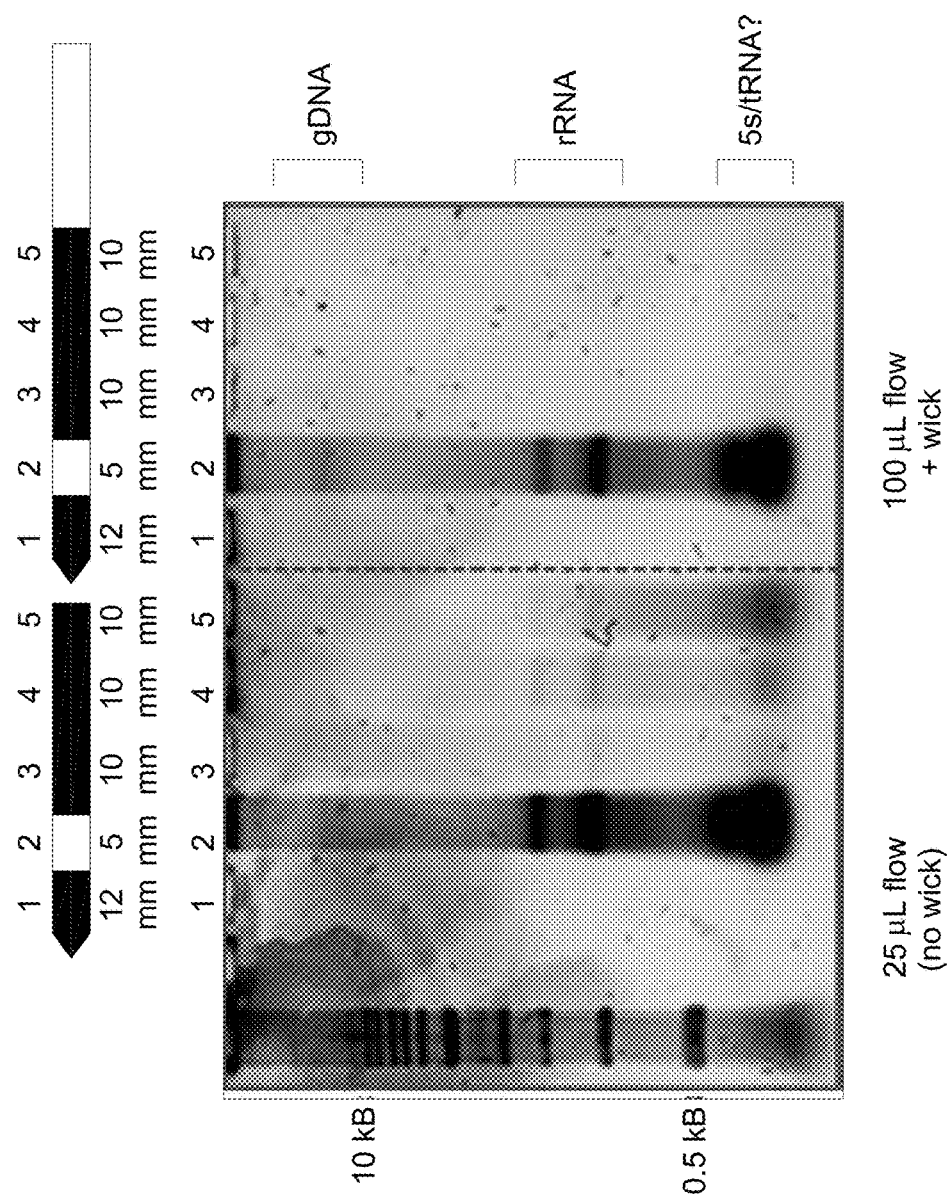
FIG. 9 illustrates a gel electrophoresis image to determine lateral flow of genomic DNA obtained in the flow diagram of FIG. 8, example 5.

Similar sections from two strips were treated as follows: 1) each section was transferred to a separate microcentrifuge tube, 2) 200 μl of TE Buffer, pH 8 (Life Technologies) was added to each tube and then vortexed, 3) the TE Buffer was recovered and further added to separate microcentrifuge tubes and centrifuged at 16,000×g for 10 minutes to pellet intact cells and debris, 4) each pre-cleared portion of TE Buffer was added back to the appropriate washed porous matrix and heated to 95° C. for 10 minutes, 5) the TE Buffer was recovered into separate microcentrifuge tubes and the nucleic acid in each tube precipitated using the DNA Extractor® Kit (Wako Chemicals, USA) according to the manufacturer's instructions, wherein as an exception, Proteinase K was omitted and 6) each pellet was resuspended and analyzed by gel electrophoresis through a 1% agarose gel in TBE Buffer (Affymetrix-USB). Following electrophoresis, the gel was stained with SYBR Gold (Life Technologies) and imaged using a Typhoon™ Variable Mode Imager (General Electric Company), which is shown in FIG. 9. As illustrated in FIG. 9, the substantial amount of genomic DNA stays in the glass fiber pad (lane 2) even after significant washing (100 μl). So, washing of target nucleic acids with an amplification buffer (without enzyme) does not result migration of the target nucleic acids on the substrate (lanes 3, 4, and 5) for both cases, the substrate with wick and without wick. The image shows that after diffusion of the amplification buffer and the TE buffer, most of the genomic DNA (molecular weight>50 kb) were positioned around the first end 11 (segment 2, FIG. 9) of the substrate (FIG. 6).

For gel electrophoresis, each small piece was placed into a separated sample well of 0.8% agarose gel. Electrophoresis was carried out with a voltage of 120 V for 45 minutes. After electrophoresis, the agarose gel was stained by 1×SYBR Green I solution for 1.5 hours and then visualized using a Typhoon™ Trio™ variable mode imager, GE Healthcare, New Jersey, USA. The Quick-Load® 1 kb DNA Ladder (New England BioLabs) was used as a DNA marker. Quick-Load® 1 kb DNA Ladder was a premixed, ready-to-load molecular weight marker containing bromophenol blue as a tracking dye. The DNA ladder consists of 10 bands: 10 kb, 8 kb, 6 kb, 5 kb, 4 kb, 3 kb, 2 kb, 1.5 kb, 1 kb and 500 bp.

Example 6

Lateral Flow Migration of Low Molecular Weight DNA Amplicons (≤50 kb)

An isothermal amplification kit was obtained from Epoch Biosciences, Inc. (Bothell, Wash.) containing primers specific for the LDH1 gene of methicillin resistant *S. aureus* (MRSA). Genomic DNA for MRSA was obtained through NIH Biodefense and Emerging Infections Research Resources Repository, NIAID, NIH. Genomic DNA from *Staphylococcus aureus*, Strain HFH-29568, NR-10314 was also used. A 5 mm diameter punch was obtained from an unmodified GF/F porous matrix (Whatman® GE Healthcare).

Figure 10A:
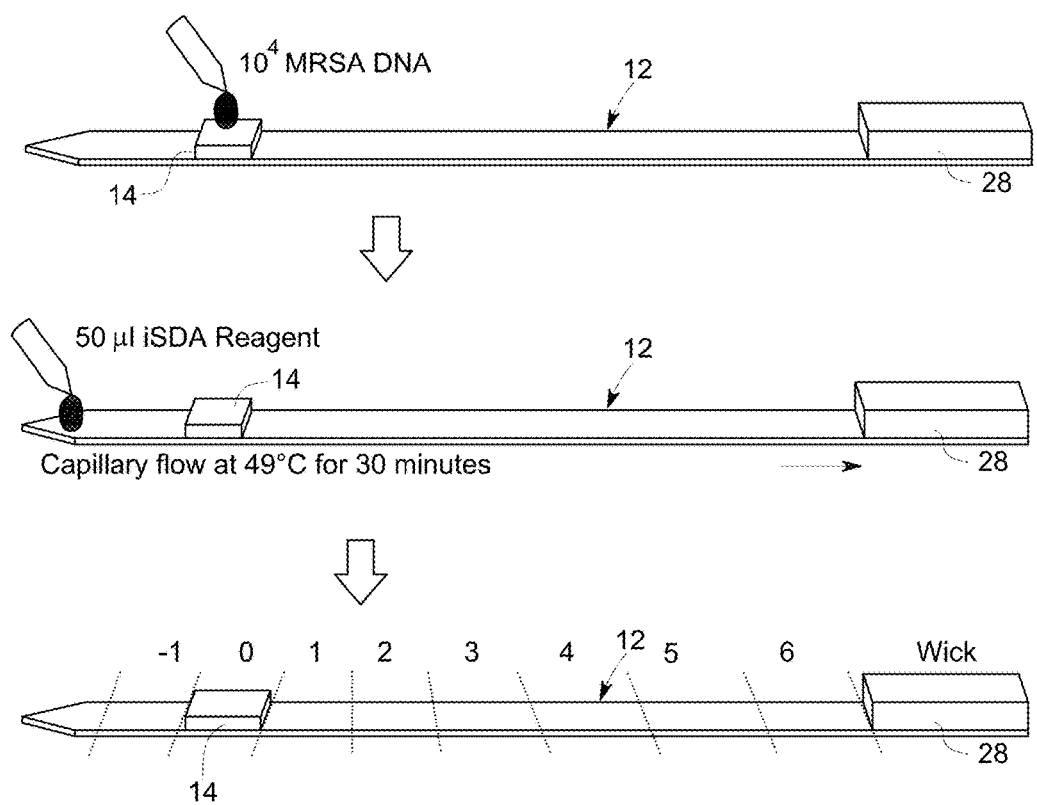
FIG. 10 A is a flow diagram that illustrates sample application, amplification and cutting the substrate into pieces for analyzing by gel electrophoresis.
Figure 10C:
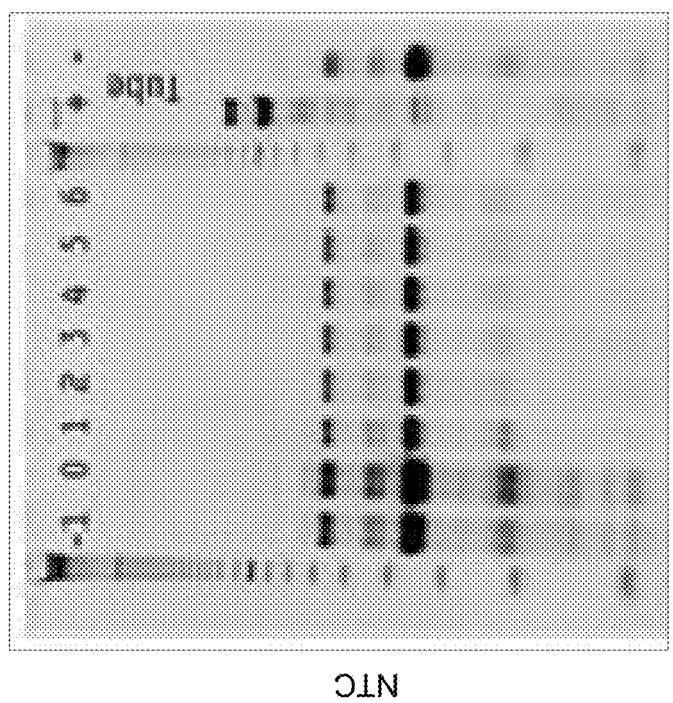
Figure 10B:
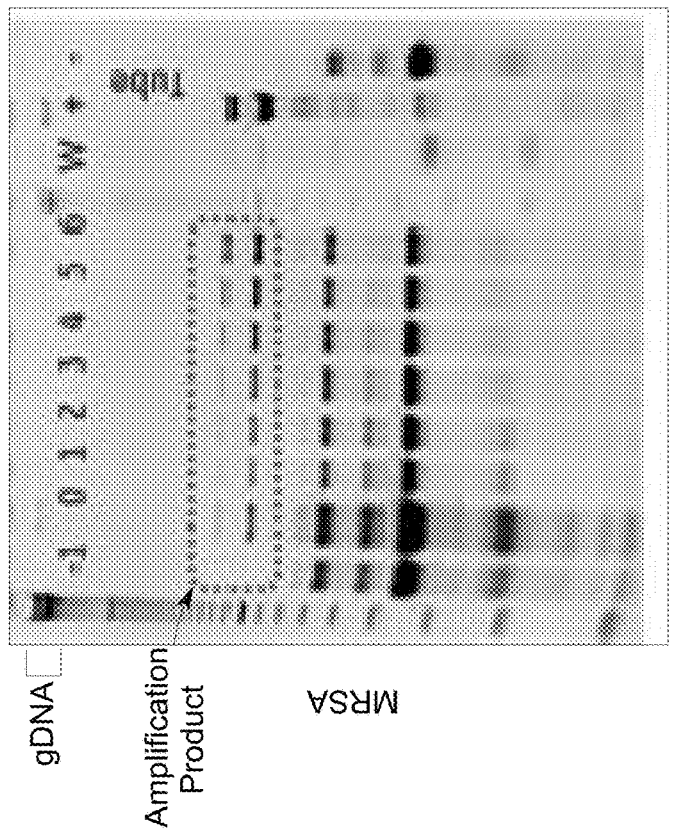

Twenty-three (23) nanograms of MRSA genomic DNA were added to the 5 mm punch and the punch was immediately assembled on a lateral flow strip 12 containing a wicking pad as found in Example 1 (as shown in FIG. 8) and also showed in FIG. 10 A. Lateral flow was initiated by applying fifty (50) microliters of amplification reaction mix containing enzymes on the pointed tip and the flow continued for 30 minutes at 49° C. At the end of the incubation period, the strip 12 was sectioned into seven (7) equal portions of 5 mm each as indicated in the work flow of FIG. 10 A.

The liquid remaining in each 5 mm section of the strip was isolated by centrifugation and a portion analyzed by electrophoresis through a 15% acrylamide TBE urea gel (Life technologies). Following electrophoresis, the gel was stained with SYBR Gold (Life Technologies) and imaged using a Typhoon™ Variable Mode Imager (General Electric Company). FIG. 10 B demonstrates (in a dotted lined box) that the expected amplification products are found in lanes 0, 1, 2, 3, 4, 5 and 6, with some appearing in the wick (lane W) compared to the gel loaded with no template control (FIG. 10 C), wherein no amplification product was determined Example 5, FIG. 9 demonstrated that the genomic DNA did not migrate during lateral flow, and this Example 6, showed increasing amounts of amplification products in each of the sections of 0 to 6 of FIG. 10 B, which established that one or more isothermal amplification reactions of MRSA DNA occurred during lateral flow, while the amplicons with lower molecular weights are determined by DNA gel electrophoresis (FIG. 10 B). The reactions were also executed in a tube with template and in another tube without template under the same conditions, as shown tube (+) and tube (−) respectively in both of the FIGS. 10 B and 10 C. A light band of genomic DNA was observed in lane 0 (above the lane numbers) and in lane for tube +. The absence of this band of genomic DNA in lanes 1 to 6 further established that the genomic DNA does not move with the amplicons during lateral flow.

Example 7

Amplification in-Flow Topology: Lateral Flow Separation of High Molecular Weight DNA and Low Molecular Weight DNA Efforts were made to evaluate amplification-in-flow topologies. A schematic representation of the amplification-in-flow is shown in FIG. 10 A.

Nitrocellulose grafted with poly(ethylene glycol) monomethyl ether methacylate (PEGMA) or NC-PEG (Pegylated Nitrocellulose) was used for this example). Polyethylene glycol methyl ether methacrylate (PEGMA) 300 grafted nitrocellulose (NC-PEG) and PEGMA 300 grafted 903 cellulose paper were fabricated by soaking the appropriate base substrate (FF60 nitrocellulose or 903 cellulose) in an aqueous solution containing 10% (w/v) PEGMA 300 (Sigma-Aldrich) and 30% (v/v) Tween 20 (Sigma-Aldrich). Excess solution was removed and the treated matrices were subjected to E-beam (AEB, Advanced Electron Beam, e-Beam unit, EBLAB-150), with operation voltage of 125 kV, and electron dosage delivery of 10 kGy. Following irradiation, the modified matrices were washed in distilled water by orbital rotating for 30 minutes. The washing steps were repeated three times. The membranes were then allowed to air dry at room temperature overnight.

An isothermal amplification kit was obtained from Epoch Biosciences, Inc. (Bothell, Wash.) containing primers specific for the LDH1 gene of methicillin resistant *S. aureus* (MRSA). Genomic DNA for MRSA was obtained through NIH Biodefense and Emerging Infections Research Resources Repository, NIAID, NIH. Genomic DNA from *Staphylococcus aureus*, Strain HFH-29568, NR-10314 was also used. Purified MRSA DNA ($10^6$ copies) was spotted onto a glass fiber pad (GF/F) bridging a gap in an NC-PEG strip. The strip was then placed into a conical tube with 50 µl of isothermal DNA amplification reaction buffer and sealed. The tube was incubated at 49° C. for 30 minutes while the isothermal DNA amplification reaction buffer flowed through the substrate (strip or test strip) and target DNA started amplified. Subsequently, the test strip was removed and cut into 5 mm segments that were then centrifuged to recover the products in each segment and analyzed via gel electrophoresis. FIG. 10 B illustrated that, below the sample pad (position −1), there is no signal in the gel, whereas on and beyond the sample pad for positions 0 through 6, the amount of amplicons increases as the distance from the sample pad and subsequently amplification time increases (the amplification products are indicated in the dotted lined box, FIG. 10 B). The band from the sample pad (position 0) appears more intense due to more product volume was recovered from the glass fiber than the NC-PEG (approximately 40% fold higher). This result demonstrates amplification-in-flow and highlights the utility of glass fiber materials when placed upstream of the flow path. When using *S. chromogenes*, it was observed that the template nucleic acids eluted from GF-F Elute with slower apparent kinetics when compared with cellulose-based FTA Elute. The delay may contribute to amplification-in-flow efficiency.

Example 8

Detection of Amplicons on the Substrate

Figure 11B:
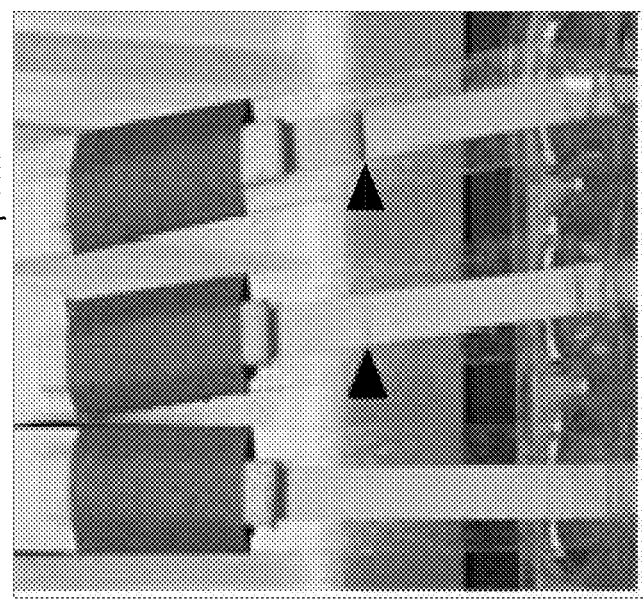
FIG. 11 A is a flow diagram that illustrates sample application, amplification on lateral flow of amplification reagent, and detection on lateral flow of detection probes on the substrate.
Figure 11A:
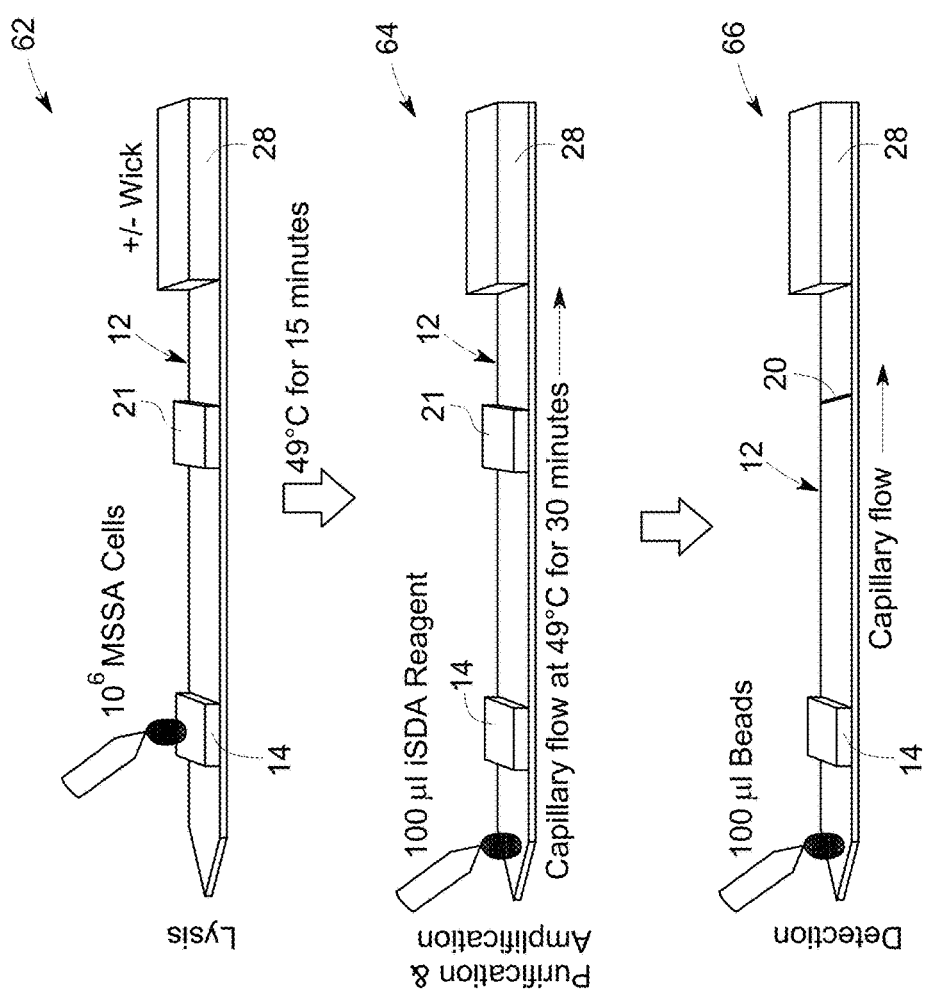

An isothermal amplification kit was obtained from Epoch Biosciences, Inc. (Bothell, Wash.) containing primers specific for the LDH1 gene of methicillin sensitive *S. aureus* (MSSA). Approximately one million cells in a 10 µl volume ($10^6$ CFU) from an overnight culture of methicillin-sensitive *Staphylococcus aureus* (*S. aureus*; ATCC) or MSSA were applied by pipet (or a swab dosed with MSSA) onto a glass fiber sample pad 62 (GF/F, containing the FTA® Elute chemistry) bridging a gap in an NC-PEG strip 12 with a test line 20 and a wick 28 (FIG. 11 A). In some examples, the test strip had an additional glass fiber pad (GF/F) 21 placed on top of the strip before the test line 20 that could be removed after amplification for analysis. The strip 64 was then heated at 49° C. for 15 minutes to facilitate faster lysis of the MSSA cells. After lysis, the strip was placed into a conical tube with 100 µl of isothermal DNA amplification (iSDA) reaction buffer and sealed 66. The strip was then incubated at 49° C. for 30 minutes as the isothermal DNA amplification reaction buffer flowed through the strip, simultaneously purifying the DNA, rinsing residual FTA® Elute chemistry from the glass fiber application site, and amplifying the ldh1 locus parallel.

The amplification in-flow was estimated which started after 25-50 µl of isothermal DNA amplification reaction buffer entered the strip 12.

Following amplification-in-flow, the strip was transferred to a second conical tube to deliver 100 µl of a "chase" buffer solution comprised of containing streptavidin coated blue polystyrene beads to that will bind to the biotin labeled probes and enable colorimetric detection of ldh1 upon capture at the test line. As shown in FIG. 11B, MSSA-dosed strips (including designs both with and without the optional glass fiber pad) showed positive results with an arrow corresponding to the bands, both in 72 and 74, while the no-template control sample without MSSA cells showed negative result 70. Similar MSSA examples repeated with cellulose-based FTA Elute rather than GF-F Elute, showed less robust performance (little to no test line development for ldh1), which demonstrates that amplification in place is slower and less efficient when using upstream cellulose materials.

The above examples demonstrated the ability of the substrate to introduce a sample directly to the substrate, lyse the cells, purify the DNA, amplify in-flow, and detect the target in a one-dimensional lateral flow device.

While the disclosure has been illustrated and described in typical embodiments, it is not intended to be limited to the details shown, since various modifications and substitutions may be made without departing in any way from the spirit of the present disclosure. As such, further modifications and equivalents of the disclosure herein disclosed may occur to persons skilled in the art using no more than routine experimentation, and all such modifications and equivalents are believed to be within the spirit and scope of the disclosure as defined by the following claims.

What is claimed is:

1. A method comprising:
   applying a sample comprising a target nucleic acid having a first molecular weight to a sample application zone of a substrate, wherein the substrate is a membrane and wherein the target nucleic acid having the first molecular weight is substantially immobilized at the sample application zone; and
   flowing a nucleic acid amplification reaction mixture comprising a deoxyribonucleic acid (DNA) polymerase across a length of the substrate through the sample application zone by a lateral flow such that a nucleic acid amplification product having a second molecular weight is formed by amplifying the target nucleic acid and is migrated away from the sample application zone by said lateral flow, wherein the first molecular weight is higher than the second molecular weight, and wherein one or more polymerase chain reaction (PCR) inhibitors are present in the sample application zone, and wherein the one or more PCR inhibitors present in the sample application zone are washed away by said flowing the nucleic acid amplification reaction mixture comprising the DNA polymerase across the length of the substrate through the sample application zone prior to said amplifying the target nucleic acid.

2. The method of claim 1, further comprising contacting the sample with a lysis reagent prior to said flowing the nucleic acid amplification reaction mixture comprising the DNA polymerase across the length of the substrate through the sample application zone, wherein the lysis reagent comprises the one or more PCR inhibitors.

3. The method of claim 2, wherein said contacting the sample with the lysis reagent is performed prior to said applying the sample to the sample application zone of the substrate.

4. The method of claim 2, wherein said contacting the sample with the lysis reagent is performed at the sample application zone of the substrate, wherein the lysis reagent is impregnated to the sample application zone of the substrate prior to said applying the sample to the sample application zone.

5. The method of claim 2, further comprising contacting the sample with a migration modifier on the sample application zone prior to said flowing the nucleic acid amplification reaction mixture comprising the DNA polymerase across the length of the substrate through the sample application zone, wherein the migration modifier comprises the one or more PCR inhibitors.

6. The method of claim 5, wherein the migration modifier comprises a chaotrope.

7. The method of claim 5, wherein the migration modifier comprises guanidinium thiocyanate.

8. The method of claim 1, wherein said flowing the nucleic acid amplification reaction mixture comprising the DNA polymerase across the length of the substrate through the sample application zone separates the target nucleic acid having the first molecular weight and the nucleic acid amplification product having the second molecular weight according to their molecular weights.

9. The method of claim 5, wherein said flowing the nucleic acid amplification reaction mixture comprising the DNA polymerase across the length of the substrate through the sample application zone further washes off the lysis reagent and the migration modifier from the sample application zone of the substrate prior to said amplifying the target nucleic acid.

10. The method of claim 1, further comprising applying a flow barrier to the substrate to prevent the migration of the nucleic acid amplification product having the second molecular weight on the substrate.

11. The method of claim 1, wherein the nucleic acid amplification product having the second molecular weight is formed by an amplification reaction occurring at the sample application zone.

12. The method of claim 11, wherein the nucleic acid amplification product having the second molecular weight is further amplified as it migrates away from the sample application zone by said lateral flow.

13. The method of claim 1, wherein the substrate comprises one or more detection probes located at the sample application zone, at a downstream of the sample application zone, or combination thereof.

14. The method of claim 13, wherein the one or more detection probes are impregnated to the substrate under dried condition, added as part of the nucleic acid amplification reaction mixture, added as a solution to the substrate, or a combination thereof.

15. The method of claim 13, further comprising detecting the nucleic acid amplification product having the second molecular weight using the detection probes.

16. The method of claim 1, further comprising capturing the nucleic acid amplification product having the second molecular weight on the substrate by a physical interaction with a capturing probe on the substrate.

17. The method of claim 16, wherein the nucleic acid amplification product having the second molecular weight is captured on the substrate by hybridization with the capturing probe that is physically bound to the substrate thereby forming a captured-amplification product.

18. The method of claim 17, further comprising flowing a solution comprising primary detection probes along the length of the substrate such that the primary detection probes bind to the captured-amplification product and thereby forming a primary detection probe-bound amplification product.

19. The method of claim 18, further comprising flowing a second solution comprising secondary detection probes along the length of the substrate such that the secondary detection probes bind to the primary detection probe-bound amplification product and thereby detecting the captured-amplification product.

20. The method of claim 1, wherein size of the target nucleic acid having the first molecular weight is about 50 kb.

21. The method of claim 1, wherein size of the target nucleic acid having the first molecular weight is in a range from about 50 kb to about 150 kb.

22. The method of claim 1, wherein the substrate is an elongated strip comprising a first end, the sample application zone, and a second end.

23. The method of claim 22, wherein the substrate further comprises a detection zone near the second end.

24. The method of claim 23, wherein a substantial amount of the nucleic acid amplification product having the second molecular weight is migrated to the detection zone by said flowing the nucleic acid amplification reaction mixture comprising the DNA polymerase across the length of the substrate through the sample application zone.

25. The method of claim 22, further comprising providing a wicking pad to a location of the substrate adjacent to the second end.

26. The method of claim 22, further comprising providing a stopping pad to a location of the substrate adjacent to the second end.

27. The method of claim 1, further comprising flowing a washing buffer through the sample application zone across the length of the substrate prior to said flowing the nucleic acid amplification reaction mixture comprising the DNA polymerase across the length of the substrate through the sample application zone.

28. The method of claim 1, wherein the target nucleic acid is a DNA.

29. The method of claim 1, wherein the membrane is made of a cellulose membrane, a nitrocellulose membrane, a modified porous nitrocellulose or a cellulose based membrane, a polyethylene glycol-modified nitrocellulose, a cellulose acetate membrane, a nitrocellulose mixed ester membrane, a glass fiber, a polyethersulfone membrane, a nylon membrane, a polyolefin membrane, a polyester membrane, a polycarbonate membrane, a polypropylene membrane, a polyvinylidene difluoride membrane, a polyethylene membrane, a polystyrene membrane, a polyurethane membrane, a polyphenylene oxide membrane, a poly(tetrafluoroethylene-co-hexafluoropropylene) membrane, or a combination thereof.

30. A method comprising:
applying a sample comprising a target nucleic acid having a first molecular weight to a sample application zone of a substrate, wherein the substrate is a membrane and wherein the target nucleic acid having the first molecular weight is substantially immobilized at the sample application zone;
laterally flowing a nucleic acid amplification reaction mixture comprising a deoxyribonucleic acid (DNA) polymerase across a length of the substrate through the sample application zone such that a nucleic acid amplification product having a second molecular weight is formed by amplifying the target nucleic acid, wherein one or more PCR inhibitors are present in the sample application zone, and wherein the one or more PCR inhibitors present in the sample application zone are washed away by said laterally flowing the nucleic acid amplification reaction mixture comprising the DNA polymerase across the length of the substrate through the sample application zone prior to said amplifying the target nucleic acid; and
separating the target nucleic acid having the first molecular weight from the nucleic acid amplification product having the second molecular weight by said laterally flowing the nucleic acid amplification reaction mixture comprising the DNA polymerase across the length of the substrate through the sample application zone such that the nucleic acid amplification product having the second molecular weight is migrated away from the sample application zone,
wherein the target nucleic acid having the first molecular weight is amplified and separated from the nucleic acid amplification product having the second molecular weight without a separate washing step, and wherein the first molecular weight is higher than the second molecular weight.

31. A method comprising:
applying a sample comprising target nucleic acids comprising a nucleic acid having a first molecular weight to a sample application zone of a substrate, wherein the substrate is a membrane and wherein the target nucleic acids comprising a nucleic acid having the first molecular weight are substantially immobilized at the sample application zone and wherein one or more nucleic acid inhibitors are present on the sample application zone;
flowing a nucleic acid amplification reaction mixture comprising a deoxyribonucleic acid (DNA) polymerase across a length of the substrate through the sample application zone by a lateral flow such that a nucleic acid amplification product having a second molecular weight is formed by amplifying the target nucleic acids and is migrated away from the sample application zone by said lateral flow, and
wherein the lateral flow of the amplification reaction mixture comprises a first portion of the lateral flow that washes away the one or more nucleic acid inhibitors from the sample application zone and a second, subsequent portion of the lateral flow that amplifies the target nucleic acids.

* * * * *